United States Patent
Rice et al.

(10) Patent No.: US 6,605,459 B2
(45) Date of Patent: Aug. 12, 2003

(54) METHODS FOR MEASURING CYSTEINE AND DETERMINING CYSTEINE SYNTHASE ACTIVITY

(75) Inventors: John Rice, Pittsboro, NC (US); Beth Lanning, Cary, NC (US); John Crawford, Raleigh, NC (US); Gordon Nye, Cary, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 09/905,290

(22) Filed: Jul. 13, 2001

(65) Prior Publication Data

US 2003/0087327 A1 May 8, 2003

(51) Int. Cl.[7] .................................................. C12N 9/88
(52) U.S. Cl. .......................... 435/232; 435/4; 435/410; 47/58.1
(58) Field of Search ................................ 435/232, 410, 435/4; 47/58.1

(56) References Cited

U.S. PATENT DOCUMENTS 5,286,803 A * 2/1994 Lindsay et al.
5,898,069 A * 4/1999 Webb et al.

FOREIGN PATENT DOCUMENTS

JP 161486 * 7/1991

OTHER PUBLICATIONS

Cooper, John et al., "Cysteine and Cystine: High—Performance Liquid Chromatography of o–Phthaladehyde Derivatives" Methods in Enzymology; vol. 143 (1987):pp. 141–143.

Wedding, R. T. et al., "Sulfide Determination: Ion–Specific Electrode"; Methods in Enzymology; vol. 143 (1987):pp. 29–31.

Smith, M. et al., "Cystine: Binding Protein Assay"; Methods in Enzymology; vol. 143 (1987):pp. 144–148.

Saito, K. et al., "Modulation of Systeine Biosynthesis in Chloroplasts of Transgenic Tobacco Overexpressing Cysteine Synthase [O–Acetylserine(thiol)–lyase]" Plant Physiology; vol. 106 (1994): pp. 887–895.

Schmidt, A. "Sulphur Metabolism"; Methods in Plant Biochemistry; vol. 3 (1990): pp. 349–354.

Molecular Probes, Inc. "Thiol–Reactive Probes" revised Nov. 8, 2000; 4849 Pitchford Ave., Eugene, OR 97402–9165.

U.S. patent application Ser. No. 09/697,225, Kloti et al., filed Oct. 26, 2000.

Yamaguchi et al., "Three Arabidopsis Genes Encoding Proteins with Differential Activities for Cysteine Synthase and β–Cyanoalanine Synthase", Plant Cell Physiology; 41; (2000): 465–476.

Gaitonde, M.K. et al., "A Spectrophotometric Method for the Direct Determination of Cysteine in the Presence of Other Naturally Occuring Amino Acids"; Biochem J. 104; (1967): pp. 627–633.

Fahey, R. C. et al. "Determination of Low–Molecular–Weight Thiols Using Monobromobimane Fluorescent Labeling and High–Performance Liquid Chromatography"; Methods in Enzymology; vol. 143; (1987): pp. 85–96.

* cited by examiner

Primary Examiner—Leon B. Lankford, Jr.
(74) Attorney, Agent, or Firm—Laura L. Kiefer; Timothy G. Hofmeyer; Deborah H. Spencer

(57) ABSTRACT

Assays, preferably high throughput assays, for determining cysteine concentration, cysteine synthase activity, and identifying herbicides, fungicides, bactericides, and insecticides. Cysteine concentration is quantitated by contacting cysteine with a coumarin dye capable of conjugating with cysteine but not to O-acetyl serine or sulfide; exciting the conjugate with UV light; and detecting fluorescent light emitted by the conjugate. Cysteine synthase activity is determined by combining O-acetyl-L-serine, sulfide and cysteine synthase to form a reaction mixture under conditions suitable for cysteine production; contacting the reaction mixture with an appropriate coumarin dye; subjecting the reaction mixture to UV light; and detecting fluorescent light emission.

27 Claims, 14 Drawing Sheets

Lane  1  2  3  4  5

Lane  1  2  3  4  5

LC/MS Analysis of Cysteine Synthase Product Formation.

Substrate alone

Cysteine Standard

Substrate and Enzyme

SEQUENCE LISTING

```
<160> NUMBER OF SEQ ID NOS: 4

<210> SEQ ID NO 1
<211> LENGTH: 35
<212> TYPE: DNA
<213> ORGANISM: Arabidopsis thaliana

<400> SEQUENCE: 1
cgggatccat ggaggaggac cggtgttcga tcaag                              35

<210> SEQ ID NO 2
<211> LENGTH: 38
<212> TYPE: DNA
<213> ORGANISM: Arabidopsis thaliana

<400> SEQUENCE: 2
ggaattctca ttgtaccggc aaattctctg cttcgtgt                           38

<210> SEQ ID NO 3
<211> LENGTH: 975
<212> TYPE: DNA
<213> ORGANISM: Arabidopsis thaliana
<220> FEATURE:
<221> NAME/KEY: misc_feature
<223> OTHER INFORMATION: AJ011603 GenBank

<400> SEQUENCE: 3
atggaggagg accggtgttc gatcaaggat gatgcaactc aattgatagg taacacccca      60
atggtatatc tgaacaacat tgtggatggt tgtgtagctc gtattgcagc taagcttgaa     120
atgatggagc cttgctctag tgtcaaggag cgaattgctt atggtatgat taaagatgca     180
gaagacaagg gattgattac tcctgggaag agcacactga ttgaggctac ctctggtaac     240
accgggattg gtttagcctt catcggtgca gctaaaggtt acaaagtggt cctcacaatg     300
```

```
cctcatcaa tgagccttga gagaaaaatc attcttttag cattaggtgc ggaggttcac      360
ctcacagatc ctagtaaagg cgttcaagga ataatcgaca aagctgaaga gatatgtagc      420
aaaaatccag atagtatcat gctagaacag ttcaaaaatc cttcaaaccc gcaaactcat      480
tatcgaacca cgggtccaga gatatggaga gactctgcag gggaagtaga catattggtt      540
gccggtgttg gaactggtgg aacgctttcc ggatcaggaa gattcctcaa ggagaagaat      600
aaagacttta aggtttatgg tgtggaacct acagaaagtg cggtaataag tggaggcaaa      660
ccgggtacac atttgatcca aggtattggg gctggactca tcccagacaa tttggatttc      720
aacgttcttg atgaagtcat ccaagtgaca agtgtggaag caattgaaac agccaaactt      780
cttgccctga agaaggatt actggtggga atatcttctg gagctgctgc agccgctgcg      840
ataaaggtgg caaagcggcc agaaaacgcc ggcaaactca tagttgtgat tttccctagc      900
ggtggggaac gttacctatc gacctcattg ttcgaatcag tcagacatga agcagagaat      960
ttgccaattc aatga                                                      975
```

<210> SEQ ID NO 4
<211> LENGTH: 324
<212> TYPE: PRT
<213> ORGANISM: Arabidopsis thaliana

<400> SEQUENCE: 4

```
Met Glu Glu Asp Arg Cys Ser Ile Lys Asp Asp Ala Thr Gln Leu Ile
1               5                   10                  15

Gly Asn Thr Pro Met Val Tyr Leu Asn Asn Ile Val Asp Gly Cys Val
            20                  25                  30

Ala Arg Ile Ala Ala Lys Leu Glu Met Met Glu Pro Cys Ser Ser Val
        35                  40                  45

Lys Glu Arg Ile Ala Tyr Gly Met Ile Lys Asp Ala Glu Asp Lys Gly
    50                  55                  60

Leu Ile Thr Pro Gly Lys Ser Thr Leu Ile Glu Ala Thr Ser Gly Asn
65                  70                  75                  80

Thr Gly Ile Gly Leu Ala Phe Ile Gly Ala Ala Lys Gly Tyr Lys Val
                85                  90                  95

Val Leu Thr Met Pro Ser Ser Met Ser Leu Glu Arg Lys Ile Ile Leu
            100                 105                 110

Leu Ala Leu Gly Ala Glu Val His Leu Thr Asp Pro Ser Lys Gly Val
        115                 120                 125

Gln Gly Ile Ile Asp Lys Ala Glu Glu Ile Cys Ser Lys Asn Pro Asp
    130                 135                 140

Ser Ile Met Leu Glu Gln Phe Lys Asn Pro Ser Asn Pro Gln Thr His
145                 150                 155                 160

Tyr Arg Thr Thr Gly Pro Glu Ile Trp Arg Asp Ser Ala Gly Glu Val
                165                 170                 175

Asp Ile Leu Val Ala Gly Val Gly Thr Gly Gly Thr Leu Ser Gly Ser
            180                 185                 190

Gly Arg Phe Leu Lys Glu Lys Asn Lys Asp Phe Lys Val Tyr Gly Val
        195                 200                 205

Glu Pro Thr Glu Ser Ala Val Ile Ser Gly Gly Lys Pro Gly Thr His
    210                 215                 220

Leu Ile Gln Gly Ile Gly Ala Gly Leu Ile Pro Asp Asn Leu Asp Phe
225                 230                 235                 240

Asn Val Leu Asp Glu Val Ile Gln Val Thr Ser Val Glu Ala Ile Glu
```

-continued

```
                    245                 250                 255
Thr Ala Lys Leu Leu Ala Leu Lys Glu Gly Leu Leu Val Gly Ile Ser
            260                 265                 270

Ser Gly Ala Ala Ala Ala Ala Ile Lys Val Ala Lys Arg Pro Glu
        275                 280                 285

Asn Ala Gly Lys Leu Ile Val Val Ile Phe Pro Ser Gly Gly Glu Arg
    290                 295                 300

Tyr Leu Ser Thr Ser Leu Phe Glu Ser Val Arg His Glu Ala Glu Asn
305                 310                 315                 320

Leu Pro Ile Gln
```

US 6,605,459 B2

METHODS FOR MEASURING CYSTEINE AND DETERMINING CYSTEINE SYNTHASE ACTIVITY

FIELD OF THE INVENTION

The invention relates generally to assays for determining cysteine concentration and cysteine synthase activity.

BACKGROUND OF THE INVENTION

Cysteine synthase (EC 4.2.99.8) is an enzyme involved in the final step of cysteine biosynthesis in a number of prokaryotic and eukaryotic organisms and catalyzes the formation of the amino acid L-cysteine from O-acetyl-L-serine (OAS) and inorganic sulfide. Inorganic sulfide is fixed by the activity of cysteine synthase. The co-factor pyridoxal phosphate converts serine to OAS, which is then converted by cysteine synthase can convert the OAS to cysteine (Saito, K., Kurosawa, M, and Murakoshi, I.).

Cysteine synthase genes have been characterized from a number of plants, and in most cases consist of a small multi-gene families, with differing cellular localization for each family member (Nakamura, T., Yamaguchi, Y., and Sano, H.). At least ten different cysteine synthase genes have been identified in *Arabidopsis thaliana*. The Arabidopsis cysteine synthase gene, AtcysC1, encodes a mitochondrial protein having both cysteine synthase activity (EC 4.2.99.8) and β-cyanoalanine synthase activity (EC 4.4.1.9). Yamaguchi et al. (2000) *Plant Cell Physiol* 41:465–476.

Commonly assigned co-pending U.S. patent application Ser. No. 09/697,225, filed Oct. 26, 2000, discloses that cysteine synthase activity is essential for plant growth and development, and can therefore be used as a herbicide target. growth and development, and can therefore be used as a herbicide target. Accordingly, it would be desirable to screen herbicide candidates for inhibition of cysteine synthase activity in high throughput assays.

Current or existing assays for cysteine synthase activity include: 1) the measurement of cysteine as a red ninhydrin complex (Gaitonde (1967) *Biochem J.* 104:627–633); 2) derivatization of the thiol group of cysteine and identification by HPLC methods (Fahey et al. (1987) *Methods in Enzymology* 143:85–96; Cooper et al. (1987) *Methods in Enzymology* 143:141–143); 3) determination of pyruvic acid after reacting cysteine with cysteine desulfhydrase (Wedding (1987) *Methods in Enzymology* 143:29–31); and by protein binding assays (Smith et al. (1987) *Methods in Enzymology* 143:144–148). However, none of these methods are readily adaptable to high throughput screening assays.

SUMMARY OF THE INVENTION

The present invention provides assays for determining cysteine concentration and cysteine synthase activity, and methods for identifying herbicides, fungicides and bactericides that function by inhibiting cysteine synthase activity.

Cysteine concentration can be quantitated by contacting cysteine with a coumarin dye capable of conjugating with cysteine but not conjugating to a significant extent with O-acetyl serine or sulfide to produce a cysteine-coumarin conjugate; exciting the conjugate with UV light; and detecting fluorescent light emitted by the conjugate. Preferred coumarin dyes are CPM and DACM Cysteine synthase activity can be determined by combining O-acetyl-L-serine, sulfide and cysteine synthase to form a reaction mixture under conditions suitable for the cysteine production; contacting the reaction mixture with an appropriate coumarin dye, for example, CPM and/or DACM; subjecting the reaction mixture to UV light; and detecting fluorescent light emission. The amount of cysteine produced can be determined by the amount of fluorescence, and the activity of the cysteine synthase determined by the amount of cysteine produced.

Methods for identifying test compounds that function as herbicides, fungicides or bactericides involve combining O-acetyl-L-serine, sulfide and a suitable plant, fungal or bacterial cysteine synthase to form a reaction mixture in the presence and absence of the test compound; contacting the reaction mixture with an appropriate coumarin dye; subjecting the reaction mixture to UV light; and detecting fluorescent light emission. The amount of the fluorescent light emission in the presence and absence of the test compound is compared. A decrease in the amount of the fluorescent light emission in the presence of the test compound indicates that the test compound is a herbicidal, fungicidal or bactericidal candidate.

BRIEF DESCRIPTION OF THE FIGURES

FIG. 5a represents the substrate alone, FIG. 5b the cysteine standard, and FIG. 5c the substrate and enzyme, where the top graph in each figure represents cysteine and the bottom graph in each figure represents OAS.

DETAILED DESCRIPTION OF THE INVENTION

Figure 1:
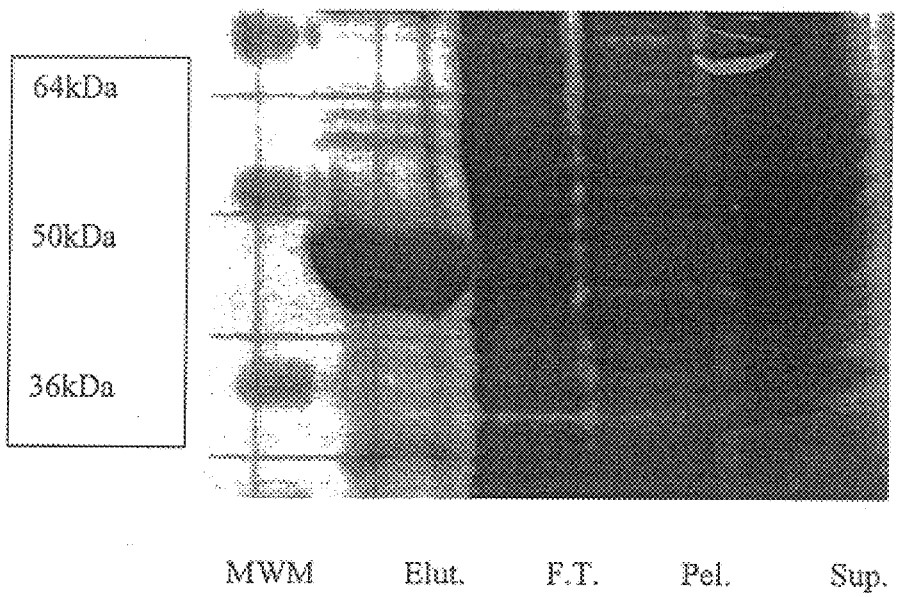
FIG. 1 is a Coomassie stained gel showing the elution of various fractions from the purification of cysteine synthase isolated from an induced *E. coli* culture. The lanes correspond to various fractions and the molecular weight versus the vertical position on the gel is displayed.

Methods and assays for detecting the presence of and/or quantitating cysteine, determining cysteine synthase activity, and identifying fungicides, bactericides and/or herbicides that function by inhibiting cysteine synthase are described. The assays are particularly suited to high throughput assay procedures. The assays are based on the detection of cysteine using thiol reactive probes (coumarin dyes such as CPM and DACM) that can be excited with ultraviolet light. The following definitions will be useful in understanding the methods and assays described herein.

Definitions

Cysteine is described as compound No. 2850 in The Merck Index, 12$^{th}$ Ed., Merck Research Laboratories, Whitehouse Station, N.J., 1996. The term cysteine is synonymous with L-cysteine, Cys, -mercaptoalanine, R-2-amino-3-mercaptopropanoic acid, 2-amino-3-mercaptopropionic acid, -amino-thiolpropionic acid, half-cysteine and thioserine.

As used herein, the term "cysteine synthase" (EC 4.2.99.8) is synonymous with "O-acetyl-L-serine (thiol) lyase", "O-acetylserine lyase", "O-acetyl-L-serine lyase", "O-acetyl-L-serine sulphydrylase" and "OAS sulfhydrylase". For the purposes of the invention, cysteine synthase refers to any enzyme that catalyzes the formation of amino acid L-cysteine and acetate from O-acetylserine and $H_2S$ and/or an inorganic sulfide. Thus, the Arabidopsis enzyme referred to as cysteine synthase C (AtCS-C, Csase C) and encoded by AtcysC1, which has both beta-cyanoalanine synthase activity and cysteine synthase activity, is included within the meaning of "cysteine synthase". Other enzymes that produce cysteine from O-acetyl serine are also contemplated for use in the assay methods.

The term "herbicide", as used herein, refers to a compound that may be used to kill or suppress the growth of at least one plant, plant cell, plant tissue or seed.

The term "fungicide", as used herein, refers to a compound that may be used to kill or suppress the growth of at least one fungus.

The term "bactericide", as used herein, refers to a compound that may be used to kill or suppress the growth of at least one species of bacteria.

The term "insecticide", as used herein, refers to a compound that may be used to kill or suppress the growth of at least one insect.

The term "selective fungicide", as used herein, refers to a compound that may be used to kill or suppress the growth of at least one fungus while not significantly adversely affecting a plant, plant cell, plant tissue or seed.

The term "selective bactericide", as used herein, refers to a compound that may be used to kill or suppress the growth of at least one bacteria while not significantly adversely affecting a plant, plant cell, plant tissue or seed.

The term "selective insecticide", as used herein, refers to a compound that may be used to kill or suppress the growth of at least one insect while not significantly adversely affecting a plant, plant cell, plant tissue or seed.

The term "inhibitor", as used herein, refers to a chemical substance that wholly or partially inactivates the enzymatic activity of cysteine synthase. The inhibitor may function by interacting directly with the enzyme, a co-factor of the enzyme, the substrate of the enzyme, or any combination thereof.

The "percent (%) sequence identity" between two polynucleotide or two polypeptide sequences is determined according to the either the BLAST program (Basic Local Alignment Search Tool; Altschul and Gish (1996) *Meth Enzymol* 266:460–480 and Altschul (1990) *J Mol Biol* 215:403–410) in the Wisconsin Genetics Software Package (Devererreux et al. (1984) *Nucl Acid Res* 12:387), Genetics Computer Group (GCG), Madison, Wis. (NCBI, Version 2.0.11, default settings) or using Smith Waterman Alignment (Smith and Waterman (1981) *Adv Appl Math* 2:482) as incorporated into GeneMatcher Plus™ (Paracel, Inc., http://www.paracel.com/html/genematcher.html; using the default settings and the version current at the time of filing). It is understood that for the purposes of determining sequence identity when comparing a DNA sequence to an RNA sequence, a thymine nucleotide is equivalent to a uracil nucleotide.

The terms "fungus", "fungi", "fungal pathogen" or "fungal phytopathogen" as used herein refer to species of the taxonomic group Myceteae and which are capable of pathogenically infecting plants or animals. For example, fungal phytopathogens include, but are not limited to, Alternaria spp., Aspergillus spp., including *As. nidulans*, Botrytis spp., Ceratocystis spp., Fusarium spp. including *F. oxysporum*, and *F. roseum*, Helminthosporum spp., Hemileia spp., *Lasiodiplodia theobromae, Magnaporthe grisea*, Meliola spp., Mucor spp., Mycosphaerella spp. including *M. graminicola*, Neurospora spp. including *N. crassa*, Oidium spp., Phoma spp., Phyllosticta spp., Sclerotina spp., Septoria spp., Trichoderma spp., Uromyces spp. and Verticillium spp. Fungal pathogens of animals and humans include, but are not limited to, Aspergillus spp., Nocardia spp., Penicillum spp., Rhizopus spp., Mucor spp., *Blastomyces dermatitidis*, Candida spp. including *C. albicans*, Saccharomyces spp., Trichosporon spp., and Trichophyton spp.

The term "pathogen" as used herein refers to an organism such as a fungus, a bacterium or protozoan capable of producing a disease in a plant or animal. The term "phytopathogen" as used herein refers to a pathogenic organism that infects a plant.

"Plant" refers to whole plants, plant organs and tissues (e.g., stems, roots, ovules, stamens, leaves, embryos, meristematic regions, callus tissue, gametophytes, sporophytes, pollen, microspores and the like) seeds, plant cells and the progeny thereof.

The term "selectively inhibiting" can also refer to the inhibition of the cysteine synthase activity of a pathogen and not to the same or greater degree of that of a host of the pathogen. The term "selectively inhibiting" can further refer to inhibiting the proliferation of a pathogen such as, but not limited to, a fungal phytopathogen whereas the proliferation of the pathogen host is not significantly inhibited.

As used herein the terms "polypeptide" and "protein" refer to a polymer of amino acids of three or more amino acids, preferably four or more amino acids, in a serial array, linked through peptide bonds. The chain may be linear, branched, circular or combinations thereof. The polypeptides may contain amino acid analogs and other modifications, including, but not limited to glycosylated or phosphorylated residues.

The term "polypeptide" includes proteins, protein fragments, protein analogues, oligopeptides and the like. The term "polypeptides" contemplates polypeptides as defined above that are encoded by nucleic acids, produced through recombinant technology, isolated or purified from an appropriate source such as a plant or fungus, or are synthesized. The term "polypeptides" further contemplates polypeptides as defined above that include chemically modified amino acids or amino acids covalently or noncovalently linked to labeling ligands.

The term "specific binding" refers to an interaction between cysteine synthase and a molecule or compound, wherein the interaction is dependent upon the primary amino acid sequence or the conformation of cysteine synthase.

As used herein, "sulfide" refers to hydrogen sulfide, inorganic sulfide or $S^{2-}$. The sulfide useful in the methods of the invention may be supplied by chemicals such as, but not limited to, hydrogen sulfide, sodium sulfide, potassium sulfide, rubidium sulfide, cesium sulfide, ammonium sulfide, beryllium sulfide, magnesium sulfide, calcium sulfide, strontium sulfide, barium sulfide and the like.

The term "nucleic acid" as used herein refers to any natural or synthetic linear and sequential arrays of nucleotides and nucleosides, for example cDNA, genomic DNA, mRNA, tRNA, oligonucleotides, oligonucleosides and derivatives thereof. For ease of discussion, such nucleic acids can be collectively referred to herein as "constructs," "plasmids," or "vectors." The term "nucleic acid" further includes modified or derivatised nucleotides and nucleosides such as, but not limited to, halogenated nucleotides such as, but not only, 5-bromouracil, and derivatised nucleotides such as biotin-labeled nucleotides.

The term "isolated nucleic acid" as used herein refers to a nucleic acid with a structure (a) not identical to that of any naturally occurring nucleic acid or (b) not identical to that of any fragment of a naturally occurring genomic nucleic acid spanning more than three separate genes, and includes DNA, RNA, or derivatives or variants thereof. The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. Isolated nucleic acid molecules of the present invention can include, for example, natural allelic variants as well as nucleic acid molecules modified by nucleotide deletions, insertions, inversions, or substitutions such that the resulting nucleic acid molecule still essentially encodes an enzyme active in the purine biosynthetic pathway.

It is advantageous for some purposes that a nucleotide sequence or a protein or polypeptide is in purified form. The term "purified" in reference to nucleic acids, proteins or polypeptides represents that the nucleic acid, protein or polypeptide has increased purity relative to the natural environment.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein or polypeptide or a portion thereof.

The term "fragment" as used herein to refer to a nucleic acid (e.g., cDNA) refers to an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art. The term "fragment" as used herein can also refer to an isolated portion of a polypeptide, wherein the portion of the polypeptide is cleaved from a naturally occurring polypeptide by proteolytic cleavage by at least one protease, or is a portion of the naturally occurring polypeptide synthesized by chemical methods well known to one of skill in the art.

The term "microarray" as used herein refers to an arrangement of distinct polynucleotides, peptides or polypeptides arranged on a substrate, e.g. paper, nylon, any other type of membrane, filter, chip, glass slide, silicone wafer, or any other suitable solid or flexible support.

I. Assay Components

Cysteine Synthase

By "cysteine synthase" is meant any enzyme which catalyzes the formation of cysteine from O-acetyl-serine and sulfide. Methods for measuring cysteine synthase activity are known to those of skill in the art and examples of suitable methods are described herein.

The cysteine synthase may have the amino acid sequence of a naturally occurring cysteine synthase found in a plant, fungus, animal or microorganism, or may have an amino acid sequence derived from a naturally occurring sequence. Preferably the cysteine synthase is a plant cysteine synthase.

By "plant cysteine synthase" is meant an enzyme that can be found in at least one plant, and which catalyzes the formation of cysteine from O-acetyl-serine and sulfide. The cysteine synthase may be from any plant, including both monocots and dicots. In one embodiment, the cysteine synthase is an Arabidopsis cysteine synthase. Arabidopsis species include, but are not limited to, *Arabidopsis arenosa, Arabidopsis bursifolia, Arabidopsis cebennensis, Arabidopsis croatica, Arabidopsis griffithiana, Arabidopsis halleri, Arabidopsis himalaica, Arabidopsis korshinskyi, Arabidopsis lyrata, Arabidopsis neglecta, Arabidopsis pumila, Arabidopsis suecica, Arabidopsis thaliana* and *Arabidopsis wallichii*. Preferably, the Arabidopsis cysteine synthase is from *Arabidopsis thaliana*, more preferably from *Arabidopsis thaliana* strain Columbia.

The cDNAs and amino acid sequences for the *A. thaliana* cysteine synthases are reported at GenBank and Embase accession numbers: emb_X80376 (Atoacly); emb_X84097 (Atcys3A); emb_X81697 (AtcysACS1); gb_AB024282 and emb_AJ010505 (AtcvsC1 or oas5; having both cysteine synthase and beta-cyanoalanine synthase activities); gb_AB024284 (AtcysD1 or oas3); gb_X81973 (mt ACS1); gb_AB003041 (cs26); gb_AB02423 (AtcysD2); gb_X81698 (cp ACS 1); gb_AJ011044 (oas6); gb_AJ011976, gb_AJ011603, gb_AJ010505 (oas5), gb_BE039257 and gb_BE037810.

The coding sequence for cysteine synthase from *Arabidopsis thaliana*, accession number AJ011603, 975 nucleotides (SEQ ID NO 3), is as follows:
atggaggaggaccggtgttcgatcaag-
gatgatgcaactcaattgataggtaacaccccaatggtatatctgaacaacattg
tggatggttgtgtagctcgtattg-
cagctaagcttgaaatgatggagcct-
tgctctagtgtcaaggagcgaattgcttatggtat gattaaagatgcagaaga-
caagggattgattactcctgggaagagcacactgattgaggctacctctggt
aacaccgggat tggtttagccttcatcggtg-
cagctaaaggttacaaagtggtcctca-
caatgccctcatcaatgagccttgagagaaaaatca ttctttttagcattaggtg
cggaggttcacctcacagatcctag-
taaaggcgttcaaggaataatcgacaaagctgaagagata tgtagcaaaaatcca-
gatagtatcatgctagaacagt-
tcaaaaatccttcaaacccgcaaactcattatcgaaccacgggtcc
agagatatggagagactctgcaggg-
gaagtagacatattggttgccggtgttggaactggtggaacgctttccggatcagg
aagattcctcaaggagaagaataaa-
gactttaaggtttatggtgtggaacctacagaaagtgcggtaataagtggaggcaa
accgggtacacatttgatccaaggtat-
tggggctggactcatcccagacaatttggatttcaacgttcttgatgaagtcatcca
agtgacaagtgtggaagcaattgaaa-
cagccaaacttcttgccctgaaagaaggattactggtgggaatatcttctggagct
gctgcagccgctgcgataaaggtg-
gcaaagcggccagaaaacgccggcaaactcatagttgtgattttccctagcggtgg
ggaacgttacctatcgacctcattgttc-
gaatcagtcagacatgaagcagagaatttgccaattcaatga The protein translation, 324 amino acids, of the above nucleotide sequence is as follows (SEQ ID NO 4):
MEEDRCSIKDDATQLIGNTPMVYLN-
NIVDGCVARIAAKLEMMEPCSSVKERI AYG-
MIKDAEDKGLITPGKSTLIEATSGNT-
GIGLAFIGAAKGYKVVLTMPSSMS
LERKIILLALGAEVHLTDPSKGVQGIID-
KAEEICSKNPDSIMLEQFKNPSNPQTH YRTTGPEI-
WRDSAGEVDILVAGVGTGGTLSGSGR-
FLKEKNKDFKVYGVEPTE
SAVISGGKPGTHLIQGIGAGLIPDNLD-
FNVLDEVIQVTSVEAIETAKLLALKEG LLVGISS-
GAAAAAIKVAKRPENAGKLIVVIFPSG-
GERYLSTSLFESVRHEAEN LPIQ In addition, the sequences of cysteine synthase cDNAs and genes from a variety of other plants and organisms are publicly available. See, for example, gb_BE611445, gb_BE610004, gb_BE608380, gb_BE555595, gb_BE348173, gb_BE348127, gb_BE330806, gb_BE329795 and gb_BE020856 (*Glycine max* cysteine synthase cDNA); gb_AI563124 (watermelon cysteine synthase cDNA); gb_AF195239 (*Pyrus pyrifolia* cysteine syhthase cDNA); gb_BE036966, gb_BE035521, gb_BE033421, gb_AI822724 and gb_AI822708 (*Mesembryanthemum crystallinum* cysteine synthase cDNA); gb_AI728743, gb_AI725847 and gb_AI725745 (*Gossypium hirsutum* cysteine synthase cDNA); gb_AW063019 (Sugar beet cysteine synthase cDNA); gb_AW164079 (*Lotus japonicus* cysteine synthase cDNA); gb_BE431668, gb_AW224722, gb_AW224770, gb_AW032102 and gb_AW031426 (*Lycopersicon esculentum* cysteine synthase); gb_D37963 and gb_D14722 (*Spinacia oleracea* cysteine synthase cDNA);

gb_AI352787 (*Brassica napus* cysteine synthase cDNA); gb_AF044173 and gb_AF044172 (*Solanum tuberosum* cysteine synthase mRNA); gb_X85803 (*Zea mays* cysteine synthase cDNA); gb_AB040503 (*Allium tuberosum* cysteine synthase cDNA); gb_AF073695, gb_AF073696 and gb_AF073697 (*Oryza sativa* cysteine synthase rcs1, rcs2 and rcs3 cDNAs); gb_AW145239 (*Physcomitrella patens* cysteine synthase cDNA); gb_U19395 (*Emericella nidulans* cysteine synthase (cysB) gene); gb_Z95395 (*Streptococcus gordonii* cysteine synthase gene); gb_X59595 (*Salmonella typhimurium* cysteine synthase cys M gene); gb_AW871292 and AW871235 (*Meloidogyne incognita* cysteine synthase mRNA); gb_AB028631 (*Entamoeba dispar* cysteine synthase 1 mRNA); gb_AB028632 (*Entamoeba dispar* cysteine synthase 2 mRNA); gb_AB006900, gb_AB000266 and gb_AB000265 (*Entamoeba histolytica* cysteine synthase mRNA); gb_AE000329 (*Escherichia coli* cysteine synthase gene); gb_AF246333 (*Acidithiobacillus ferroxidans* cysteine synthase gene); gb_U93874 (*Bacillus subtilis* cysteine synthase); gb_AB028629 (*Clostridium perfringens* cysteine synthase); gb_AJ389044, gb_AJ389018 and gb_AJ388898 (*Medicago truncatula* cysteine synthase cDNA); gb_AF 186381 (*Bacillus thermolevorans* cysteine synthase cDNA); and gb_AW720774 (*Chlamydomaonas reinhardtii* cysteine synthase cDNA). All of the above cysteine synthase cDNA sequences may be used as probes to isolate cysteine synthase cDNAs or genes from additional organisms, and to synthesize cysteine synthase polypeptides.

In various embodiments, the cysteine synthase is from barnyard grass (*Echinochloa crus-galli*), crabgrass (*Digitaria sanguinalis*), green foxtail (*Setana viridis*), perennial ryegrass (*Lolium perenne*), hairy beggarticks (*Bidens pilosa*), nightshade (*Solanum nigrum*), smartweed (*Polygonum lapathifolium*), velvetleaf (*Abutilon theophrasti*), common lambsquarters (*Chenopodium album* L.), *Brachiara plantaginea, Cassia occidentalis, Ipomoea aristolochiaefolia, Ipomoea purpurea, Euphorbia heterophylla*, Setaria spp, *Amaranthus retroflexus, Sida spinosa, Xanthium strumarium* and the like.

Fragments of a plant cysteine synthase may be used in the assays described herein. The fragments comprise at least 10 consecutive amino acids of a plant cysteine synthase. Preferably, the fragment comprises at least 15, 20, 25, 30, 35, 40, 50, 60, 70, 80, 90 or at least 100 consecutive amino acids residues of a plant cysteine synthase. Most preferably, the fragment comprises at least 10 consecutive amino acid residues of an Arabidopsis cysteine synthase. Preferably, the fragment contains an amino acid sequence conserved among plant cysteine synthases. Such conserved fragments are identified in Rolland et al. (1993) *Biochem J* 293:829–833. Those skilled in the art could identify additional conserved fragments using sequence comparison software.

Polypeptides having at least 80% sequence identity with a plant cysteine synthase are also useful in the methods of the invention. Preferably, the sequence identity is at least 85%, more preferably the identity is at least 90%, most preferably the sequence identity is at least 95%.

In addition, it is preferred that the polypeptide has at least 50% of the activity of a plant cysteine synthase. More preferably, the polypeptide has at least 60%, at least 70%, at least 80% or at least 90% of the activity of a plant cysteine synthase. Most preferably, the polypeptide has at least 50%, at least 60%, at least 70%, at least 80% or at least 90% of the activity of the *A. thaliana* 'Columbia' cysteine synthase of SEQ ID NO:4.

Preferably, the activity of the polypeptide is compared to the activity of the Arabidopsis cysteine synthase polypeptide.

Fungal and/or bacterial cysteine synthases can also be used in the assays. A suitable fungal cysteine synthase, for example, that can be the target of a test compound is that of the fungus *M. grisea*, or derivatives or truncated versions thereof.

Cysteine O-acetyl-serine and Sulfide

Cysteine, O-acetyl serine and various sources of sulfide, as defined above, are readily available from commercial sources, including Aldrich Chemicals.

Dyes

Any coumarin dye capable of conjugating with cysteine but which does not conjugate to an appreciable degree with the cysteine precursors (sulfide and OAS) can be used in the assays described herein. Preferred coumarin dyes are CPM and DACM. Representative coumarin dyes are described, for example, in U.S. Pat. No. 5,286,803 to Lindsay et al., the contents of which are hereby incorporated by reference. Lindsay discloses various coumarin dyes and side-chain coumarin dye-substituted polymers which exhibit nonlinear optical properties. Coumarin dyes include alkylaminocoumarin carboxamides, and can include functional hydroxyl groups and can be chemically attached to vinyl monomers such as methacrylic acid. Those dyes which are chemically attached to vinyl monomers can be co-polymerized, e.g. with acrylic monomers to produce coumarin dye-containing polymers. Examples of other coumarin dyes that can be used include, but are not limited to, coumarins 1, 6,7,30,47, 120, 460, 515 and 535.

Solutions/Media

In those embodiments of the assays that are cell-free assays, any media in which the enzyme is active and in which the reactants and products are soluble can be used. Preferred solutions are buffered solutions, more preferably, solutions buffered to about physiological pH. The solutions can include DMSO or other water-soluble organic solvents that can assist with long term storage of the cysteine synthase at reduced temperatures. Examples of suitable aqueous solutions containing DMSO that can be used are described in more detail in the Examples.

In those embodiments of the assays that use whole cells or tissues, any cell culture media capable of sustaining the viability of the cells and also solubilizing the reactants and products can be used. Examples of cell culture media are well known to those of skill in the art.

Compounds

Various types of compounds can be screened for their potential ability to inhibit cysteine synthase. Examples include, but are not limited to, enzymes, amino acids and derivatives thereof, proteins (including more than about 70 amino acids), peptides (including between 2 and 70 amino acids), natural and synthetic saccharides, genetic material, viruses, bacteria, vectors and small molecules (molecules with molecular weights less than about 1000).

Compound Libraries

The compounds can be present in combinatorial or other compound libraries, for example, lead generation and/or lead optimization libraries. For purposes of this invention, lead generation libraries are relatively large libraries that contain potential lead compounds, and lead optimization libraries are developed around compounds identified as potential leads by assaying lead generation libraries. Such libraries typically include a large number of compounds, include at least two compounds, and can include upwards of tens of thousands of compounds.

Logically arranged collections of potentially active herbicidal, bactericidal and/or fungicidal compounds can be evaluated using the high throughput bioassays described herein, such that structure-reactivity relationships (SARs) can be obtained. Methods for arranging compounds to be assayed in logical arrangements are known to those of skill in the art, and described, for example, in U.S. Pat. No. 5,962,736 to Zambias et al., the contents of which are hereby incorporated by reference. In one embodiment, the compounds are added to multi-well plates in the form of an "array," which is defined herein as a logical positional ordering of compounds in Cartesian coordinates, where the array includes compounds with a similar core structure and varying substitutions.

By placing the compounds in a logical array in multi-tube arrays or multi-well plates, the herbicidal, bactericidal or fungicidal effect of individual compounds can be evaluated, and compared to that of structurally similar compounds to generate SAR data.

Relational Databases

In one embodiment, the identity and activity of the compounds are stored on a relational database. By evaluating the SAR data, lead compounds can be identified, and lead optimization libraries designed. The logically arranged arrays can be evaluated in a manner which automatically generates complete relational structural information such that a positive result provides: (1) information on a compound within any given spatial address on the multi-well plates and (2) the ability to extract relational structural information from negative results in the presence of positive results.

II. Preparation of Recombinant Cysteine Synthase

Cysteine synthase can be produced in purified form by any known conventional techniques. For example, the DNA molecules encoding cysteine synthase can be incorporated into cells using conventional recombinant DNA technology. The DNA molecules can be inserted into an expression system to which the DNA molecules are heterologous (i.e., not normally present) or where over-expression of the cysteine synthase protein is desired.

For expression in heterologous systems, the heterologous DNA molecule is inserted into the expression system or vector in proper sense orientation and correct reading frame. The vector contains the necessary elements for the transcription and translation of the inserted protein-coding sequences. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

The nucleic acid sequences, or derivatives or truncated variants thereof can, for example, be introduced into viruses such as vaccinia virus. Methods for making a viral recombinant vector useful for expressing the cysteine synthase protein are analogous to the methods disclosed in U.S. Pat. Nos. 4,603,112; 4,769,330; 5,174,993; 5,505,941; 5,338,683; 5,494,807; 4,722,848; Paoletti, E. (Proc. Natl. Acad. Sci. 93, 11349–11353 (1996)), Moss (Proc. Natl. Acad. Sci. 93, 11341–11348 (1996)), Roizman (Proc. Natl. Acad. Sci. 93, 11307–11302 (1996)), Frolov et al. (Proc. Natl. Acad. Sci. 93, 11371–11377 (1996)), Grunhaus et al. (Seminars in Virology 3, 237–252 (1993)) and U.S. Pat. Nos. 5,591,639; 5,589,466; and 5,580,859 relating to DNA expression vectors, inter alia; the contents of which are incorporated herein by reference in their entireties.

Recombinant molecules can be introduced into cells via transformation, particularly transduction, conjugation, mobilization, or electroporation. The DNA sequences are cloned into the vector using standard cloning procedures in the art, as described by Maniatis et al. (Molecular Cloning: A Laboratory Manual, Cold Springs Laboratory, Cold Springs Harbor, N.Y. (1982)), which is hereby incorporated by reference in its entirety.

A variety of host-vector systems can be used to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; vertebrate cell systems infected with virus (e.g., vaccinia virus, adenovirus, etc.); insect cell systems infected with virus (e.g., baculovirus) or fungal embryonic cells inoculated with the recombinant, nucleic acid. The expression elements of these vectors vary in their strength and specificities. Depending upon the host-vector system used, any one of a number of suitable transcription and translation elements can be used.

Different genetic signals and processing events control many levels of gene expression (e.g., DNA transcription and messenger RNA (mRNA) translation). Transcription of DNA is dependent upon the presence of a promoter that is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals cannot be recognized in or cannot function in a prokaryotic system, and further, prokaryotic promoters are not recognized and do not function in eukaryotic cells.

Similarly, translation of mRNA in prokaryotes depends upon the presence of the proper prokaryotic signals that differ from those of eukaryotes. Efficient translation of mRNA in prokaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer (Methods Enzymol. 68, 473 (1979)), which is hereby incorporated by reference in its entirety.

Promoters vary in their "strength" (i.e. their ability to promote transcription). For the purposes of expressing a cloned gene, it is desirable to use strong promoters to obtain a high level of transcription and hence, expression of the gene. Depending upon the host cell system used, any one of a number of suitable promoters can be used. For instance, when cloning in E. coli, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, can be used to direct high levels of transcription of adjacent DNA segments. Additionally, a hybrid trp-lacUV5 (tac) promotor or other E. coli promoters produced by recombinant DNA or other synthetic DNA techniques can be used to provide for transcription of the inserted gene.

Bacterial host cell strains and expression vectors can be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-β-D-galactoside). A variety of other operons, such as trp, pro, etc., are under different controls.

Once the isolated DNA molecule has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

Recombinant expression vectors can be designed for the expression of the encoded proteins in prokaryotic or eukaryotic cells. The prokaryotic expression system can comprise the host bacterial species *E. coli, B. subtilis* or any other host cell known to one of skill in the art. Useful vectors can comprise constitutive or inducible promoters to direct expression of either fusion or non-fusion proteins. With fusion vectors, a number of amino acids are usually added to the expressed target gene sequence such as, but not limited to, a protein sequence for thioredoxin. A proteolytic cleavage site can further be introduced at a site between the target recombinant protein and the fusion sequence. Additionally, a region of amino acids such as a polymeric histidine region can be introduced to allow binding to the fusion protein by metallic ions such as nickel bonded to a solid support, and thereby allow purification of the fusion protein. Once the fusion protein has been purified, the cleavage site allows the target recombinant protein to be separated from the fusion sequence. Enzymes suitable for use in cleaving the proteolytic cleavage site include, but are not limited to, Factor Xa and thrombin. Fusion expression vectors that can be useful in the present invention include pGex (Amrad Corp., Melbourne, Australia), pRIT5 (Pharmacia, Piscataway, N.J.) and pMAL (New England Biolabs, Beverly, Mass.), that fuse glutathione S-transferase, protein A, or maltose E binding protein, respectively, to the target recombinant protein.

Expression of unfused foreign genes in *E. coli* can be accomplished with recombinant vectors including, but not limited to, the *E. coli* expression vector pUR278 as described in Ruther et al. (E.M.B.O.J. 2, 1791–1794 (1983)), incorporated herein by reference in its entirety. Using the pUR278 vector, the nucleotide sequence coding for the prol gene product can be ligated in frame with the lacV coding region to produce a fusion protein.

Expression of a foreign gene can also be obtained using eukaryotic hosts such as mammalian, yeast or insect cells. Using eukaryotic vectors permits partial or complete post-translational modification such as, but not only, glycosylation and/or the formation of the relevant inter- or intra-chain disulfide bonds. Examples of vectors useful for expression in the yeast *Saccharomyces cerevisiae* include pYepSecl as in Baldari et al., (E.M.B.O.J. 6, 229–234 (1987)) and pYES2 (Invitrogen Corp., San Diego, Calif.), incorporated herein by reference in their entireties.

Baculovirus vectors are also available for the expression of proteins in cultured insect cells (F9 cells). Using recombinant Baculovirus vectors can be, or is, analogous to the methods disclosed in Richardson C. D. ed., (1995), "Baculovirus Expression Protocol" Humana Press Inc.; Smith et al. (Mol. Cell. Biol. 3, 2156–2165 (1983)), Pennock et al., (Mol. Cell. Biol. 4, 399–406 (1984)) and incorporated herein by reference in their entireties.

III. Assay Methods

Methods for Quantitating Cysteine

The amount of cysteine in a sample can be determined by contacting cysteine with an appropriate coumarin dye, for example, CPM and/or DACM, to produce a cysteine-coumarin conjugate; exciting the conjugate with UV light; and detecting fluorescent light emitted by the conjugate. The amount of cysteine is then calculated based on the amount of detected fluorescence.

Methods for Determining Cysteine Synthase Activity

Cysteine synthase activity can be determined by in cell-free assays using isolated cysteine synthase, preferably isolated recombinant cysteine synthase, more preferably a water-soluble recombinant cysteine synthase. The cell-free assays involve combining O-acetyl-L-serine, sulfide and cysteine synthase to form a reaction mixture under conditions suitable for producing cysteine, contacting the reaction mixture with an appropriate coumarin dye such as CPM and/or DACM; and subjecting the reaction mixture from step (b) to UV light and detecting fluorescent light emission. The amount of cysteine produced can be determined by the amount of fluorescence, and the activity of the cysteine synthase determined by the amount of cysteine produced.

Cysteine synthase activity can also be determined by in cell-based assays using the cysteine synthase present in the cells, and the control amount of cysteine produced by the cell determined using a control. Cells can be lysed and the cysteine measured in the lysate.

Methods for Identifying Herbicide/Bactericide/Fungicide Candidates

Test compounds suitable as herbicide, bactericide or fungicide candidates can be identified by combining O-acetyl-L-serine, sulfide and an appropriate cysteine synthase from a plant, fungal or bacterial source to form a reaction mixture in the presence and absence of the test compound. The reaction mixtures are contacted with an appropriate coumarin dye such as CPM and/or DACM and subjected to UV light. The fluorescent light emission is detected and the amount of the fluorescent light emission in the presence and absence of the test compound is compared. A decrease in the amount of the fluorescent light emission in the presence of the test compound indicates that the test compound is a herbicide, bactericide or fungicide candidate.

Methods of Controlling Plant Growth

Chemicals, compounds or compositions identified by the above methods as modulators of plant cysteine synthase expression or activity can then be used to control plant growth. For example, compounds that inhibit plant growth can be applied to a plant or expressed in a plant, in order to prevent plant growth. Thus, the invention provides a method for inhibiting plant growth, comprising contacting a plant with a compound identified by the methods of the invention as having herbicidal activity.

Herbicides and herbicide candidates identified using the methods described herein can be used to control the growth of undesired plants, including both monocots and dicots. Examples of undesired plants include, but are not limited to barnyard grass (*Echinochloa crus-galli*), crabgrass (*Digitaria sanguinalis*), green foxtail (*Setana viridis*), perennial ryegrass (*Lolium perenne*), hairy beggarticks (*Bidens pilosa*), nightshade (*Solanum nigrum*), smartweed (*Polygonum lapathifolium*), velvetleaf (*Abutilon theophrasti*), common lambsquarters (*Chenopodium album* L.), *Brachiara plantaginea, Cassia occidentalis, Ipomoea aristolochiaefolia, Ipomoea purpurea, Euphorbia heterophylla*, Setaria spp, *Amaranthus retroflexus, Sida spinosa, Xanthium strumarium* and the like.

Methods of Controlling Fungal or Bacterial Infection

Chemicals, compounds or compositions identified by the above methods as modulators of fungal or bacterial cysteine synthase expression or activity can then be used to control fungal or bacterial infection. For example, compounds that inhibit fungal growth can be applied to an animal or plant or expressed in a plant, in order to prevent or treat fungal infections.

Accordingly, fungal infections can be treated or prevented by contacting a plant or animal with a compound identified by the methods of the invention as having herbicidal activity.

Methods of Selectively Inhibiting Cysteine Synthase

Methods for identifying compounds that can selectively inhibit cysteine synthase activity are particularly useful. Compounds that selectivity inhibit plant, fungal or bacterial cysteine synthase activity, in preference to other cysteine synthase activity, can be used to identify compounds useful to target fungi and/or bacteria over plants, plants over fungi and/or bacteria, or bacteria over fungi and/or plants.

A suitable cysteine synthase for use in the assays is derived from *Arabidopsis thaliana*, wherein the cysteine synthase has the amino acid shown in sequence SEQ ID NO: 4, or a derivative or truncated version thereof In one embodiment, potential herbicidal compounds are evaluated with respect to their ability to inhibit cysteine synthase in bacteria, fungi or insects that adversely affect plants. Ideally, the compounds either do not adversely affect the cysteine synthase in the plants of interest, or do so to a lesser degree. This can be determined, for example, by preparing or obtaining an appropriate library of compounds, screening them for activity against a suitable plant cysteine synthase, and then screening them for activity against a suitable fungal or bacterial cysteine synthase. Compounds that are selective for the fungus or bacteria over the plant of interest can then be identified.

Methods of Inhibiting the Formation of Cysteine Synthase

The total amount of cysteine produced by a plant, fungus or bacteria can be altered by affecting the formation of cysteine synthase itself or by modulating cysteine synthase activity after the cysteine synthase is formed. Cell free assays use the cysteine synthase and focus on compounds that inhibit the activity of the cysteine synthase. Cell based assays can be used to identify compounds that effect cysteine synthase formation as well as compounds that effect the cysteine synthase once formed. Compounds identified in the cell based assays can be used to alter cysteine synthase formation, or alter the cysteine synthase that is formed. Since enzyme production is controlled by DNA, nucleic acids are one example of compounds that can be used to alter cysteine synthase expression.

Accordingly, isolated "antisense" nucleic acids can be used as "antisense" fungicides, bactericides and/or herbicides. An antisense construct can be delivered, for example, as an expression plasmid that when transcribed in the fungal, bacterial or plant cell, produces RNA that is complementary to at least a unique portion of the cellular mRNA which encodes a cysteine synthase protein. Alternatively, the antisense construct can be an oligonucleotide probe that is generated ex vivo and, when introduced into the fungal cell, inhibits expression by hybridizing with the mRNA and/or genomic sequences encoding one of the subject cysteine synthase proteins.

IV. High Throughput Methodology

The assays used to measure cysteine synthase activity can be generated in many different forms and include assays based on cell-free systems, e.g. purified proteins or cell lysates, as well as cell-based assays that use intact cells. In order to test libraries of compounds and natural extracts, high throughput assays are desirable to maximize the number of compositions surveyed in a given period of time.

Assays performed in cell-free systems, such as can be derived with purified or semi-purified proteins or polypeptides thereof or with lysates, are often preferred as "primary" screens in that they can be generated to permit rapid development and relatively easy detection of an alteration in a molecular target which is mediated by a test composition. The effects of cellular toxicity and/or bioavailability of the test composition can be generally ignored in the in vitro system, the assay instead being focused primarily on the effect of the drug on the molecular target as can be manifested in an alteration of binding affinity with other proteins or change in enzymatic properties of the molecular target.

Potential inhibitors of the enzyme activity can be detected in a cell-free assay generated with an isolated cysteine synthase enzyme in a cell lysate or an isolated cysteine synthase enzyme purified from the lysate. Some of the compounds will bind directly to the target polypeptide, and these can be identified using competitive and non-competitive binding assays, Scatchard plot determinations, and the like.

Microarrays can be used to test a large number of compounds using a minimum amount of laboratory space. The term "microarray" as used herein refers to an arrangement of distinct polynucleotides or peptides or polypeptides arranged on a substrate, e.g. paper, nylon, any other type of membrane, filter, chip, glass slide, silicone wafer, or any other suitable solid or flexible support.

Multiwell plates, for example, 96- and 384-well plates, can be used to run multiple assays at the same time. Liquid handlers, for example, those sold by Tecan, can be used to add repeatable amounts of small volumes of liquid to each of the wells. High throughput analytical equipment can be used to analyze multiple samples in a relatively short amount of time. Relational databases, as such are known in the art, can be used to store information about the structure and activity of the compounds that are analyzed.

The conditions for one embodiment of the high-throughput bioassays described herein are as follows: A fluorometric high throughput assay for detecting cysteine synthase inhibitory activity was developed in 384-well microtiter plate format. Recombinant cysteine synthase from both E coli and baculovirus sources are suitable and can be used in the assays. The substrates O-acetyl serine ((Km was calculated at around 500 $\mu$M) and sulfide (100 $\mu$M or higher) were mixed in a buffer solution (i.e., phosphate buffer, pH 7.5) containing 50–1,000 ng of recombinant protein in a total volume of about 50 $\mu$l.

The bioassays are preferably performed using robotic systems such as are commonly used in combinatorial chemistry. Enzyme inhibition can be measured via fluorescent detection. Fluorescence readings can be taken at an excitation wavelength of 340 nm and an emission wavelength of 465 nm, for example, on a Tecan Ultra reader (Tecan), which supports all plate types (from 6 well up to 1536 well), has a relatively short measurement time for all plate formats: <1 min (uHTS), and has a wavelength range from 230 nm to 850 nm.

Combinations of stock solutions at standard concentration can be prepared for the automated steps of the synthesis. The compounds to be evaluated can be solubilized in any suitable solvent, for example, dimethyl sulfoxide (DMSO) and pre-transferred to a multi-well plate (for example, a 96 or 384 well assay plate) to yield the indicated final concentration of compound.

The number and percentage (i.e., "hit rate") of compounds in each array that produce greater than 50% inhibition can be determined for each array.

The percentage of inhibition can be plotted against the logarithm of inhibitor concentration, and the inhibitor concentration at 50% inhibition can be determined ($IC_{50}$).

The discovery of potential herbicides, bactericides and/or fungicides can be accelerated by integrating high throughput testing with high throughput synthesis and/or by using logically-ordered, spatially addressable arrays.

Methods of Preparing and Arranging Combinatorial Libraries

Combinatorial libraries of compounds to be evaluated using the bioassays described herein can be prepared using known methods, for example, by reacting components to form a molecular core structure and structural diversity elements. Thus, during synthesis, "components" are used to make the "members" or "individual compounds" of an array, and the terms "molecular core" (or "molecular core structure") and "diversity element" (or "structural diversity element") are used herein to describe the parts of the completed compounds of an array.

The members of the new arrays can be constructed from a wide variety of reaction components. Each component can form a part or all of a molecular core structure or structural diversity element. Thus, components can be added to reactive sites on a preexisting molecular core structure to form or attach structural diversity elements.

On the other hand, the molecular core structure and the structural diversity elements can, in some cases, be formed from a combination of two or more components. For example, one component can include a portion of a molecular core structure and also a partial or complete structural diversity element, while a second component can include the remainder of the molecular core structure together with any remaining structural diversity elements.

The methods described above can also be used to synthesize libraries of compounds to be used in the construction of an array. Laboratory-scale robotic devices can be used to automate the unit operations of the organic chemical syntheses. The analysis of the synthesis products can be integrated into automated synthesis as an on-line quality control function, with automated data acquisition and storage, and historical process analysis.

A 96-well or 384-well microtiter-type spatial format plate can serve as the foundation for managing both high throughput screening data and chemical synthesis data. Organic compounds arrayed in alpha-numerically registered 96-well or 384-well plates can be specified by descriptors derived from row, column, and plate numbers. The descriptors are ideally suited for electronic storage and retrieval from chemical and biological databases. This format allows high throughput bioassays for inhibiting cysteine synthase to be performed with the chemical arrays and provides insights into structure activity relationships of the chemical arrays.

The present invention will be better understood with reference to the following on-limiting examples.

EXAMPLE 1

Generation of Recombinant Cysteine Synthase

Inorganic sulfide is fixed in a number of prokaryotic and eukaryotic organisms by the activity of cysteine synthase. Cysteine synthase [EC 4.2.99.8] catalyzes the formation of L-cysteine from the substrates O-aceytl-L-serine and sulfide. In a number of plants, cysteine synthase has been found to consist of small multigene families, with differing cellular localization for each family member (Nakamura, T., Yamaguchi, Y., and Sano, H.). Arabidopsis has at least three different cysteine synthase genes, two of which clearly encode for cysteine synthase. One sequence has been proposed to be a beta-cyanoalanine synthase [EC4.4.1.9] even though it appears to have cysteine synthase activity. Antisense technology can be used to suppress cysteine synthase activity in Arabidopsis. The suppressed cysteine synthase activity shows that cysteine synthase activity is essential for Arabidopsis growth and development.

This experiment illustrates the generation of suitable recombinant cysteine synthase proteins for use in the assays described herein. It should be noted that other cysteine synthase proteins than those specifically described herein can be used in the assays.

Cloning strategy for cysteine synthase (CS): Total RNA was collected from 14 day old *Arabidopsis thaliana* seedlings using published protocols and reagents (Trizol) from Life Technologies, Inc. (Rockville, Md.). One hundred nanograms each of custom oligos, CGGGATCCATGGAG-GAGGACCGGTGTTCGATCAAG (SEQ ID NO 1) and GGAATTCTCATTGTACCGGCAAAT-TCTCTGCTTCGTGT (SEQ ID NO 2), were incubated with 1 µg of total RNA in a reverse transcriptase polymerase chain reaction (RT-PCR) kit (Life Technologies) according to the manufacturer's recommendations. The resulting PCR product, and plasmid pET30a(+) (Novagen, Madison, Wis.), were digested with restriction endonucleases BamH I and EcoR I, as directed by the manufacturer (Life Technologies). Ligation of these two linear DNAs into the resulting recombinant clone pET30/CS was accomplished by following instructions included with T4 DNA ligase (Life Technologies). The integrity of the above clone was verified by DNA sequence analysis.

Methods employed to express the CS gene in *E. coli*: Clone pET30/CS was transformed into a proprietary bacterial strain, *E. coli* BL21(DE3)lysS (Novagen), following the manufacturers instructions. Transformed bacteria were grown in LB liquid media (including 10 grams each of tryptone and NaCl; 5 grams of yeast extract; $H_2O$ to one liter) at 37° C. to an optical density of 0.6 at 600 nm. At that point, isopropylthio-beta-galactoside was added to a final concentration of 1 millimolar and the culture was incubated at 23° C. for 16 additional hours. Bacteria were pelleted via centrifugation, the supernatant discarded, and the pellet frozen to −80 C. Pellets from ~250 ml of culture were lysed in 10 ml of BugBuster lysis solution (Novagen) with 20 µl of benzonase following the manufacturers suggested protocol. The cell lysis was clarified by centrifugation at 15,000×g for 10 minutes.

Figure 2:
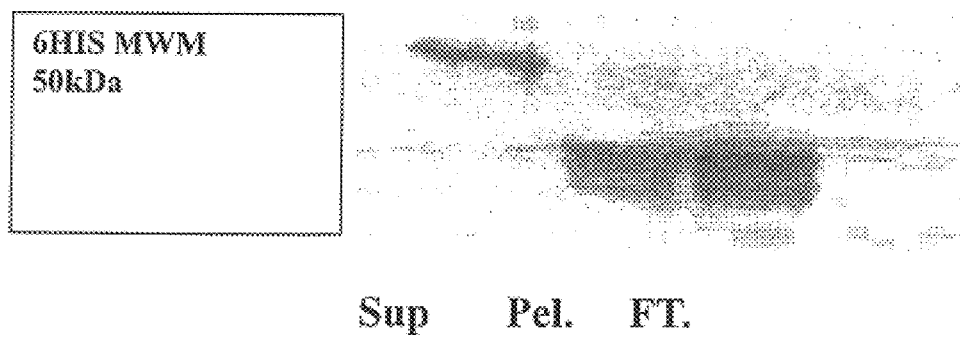
FIG. 2 is a western blot of cysteine synthase derived from the *E. coli* purification, as shown in Example 1.

Cysteine synthase from the induced *E. coli* culture was purified using the protocol described below. A Coomassie stained gel of the various fractions from the purification is shown in FIG. 1. The gel lanes correspond to the following samples—1) molecular weight marker (MWM). 2) elution (Elut.). 3) column flow through (F.T.). 4) pellet fraction (Pel.). 5) supernate fraction (Sup.). About 40 mg of protein was typically recovered per liter of fermentation product. The collected supernatant contained soluble cysteine synthase (CS) protein, as determined by western blot analysis (FIG. 2).

Methods employed to express the CS gene in Baculovirusi: Both the pET30/CS clone and baculovirus expression vector pFastBac HTb (Life Technologies) were digested with restriction enzymes BamH I and EcoR I. A 983 nucleotide fragment, containing the intact CS gene cassette, was recovered from the digested pET30/CS and joined via 1T4 DNA ligase (Life Technologies) to digested pFastBac HTb, creating pFB/CS. This construct was purified, DNA sequence verified, and used to transform DH10Bac *E. coli* competent cells (Life Technologies). DNA from overnight transformed *E. Coli* cultures was purified using the Concert DNA purification system (Gibco) and transfected into Sf-9 insect cells using Cellfectamine reagent (Gibco) following the manufacturer's protocol. Recombinant virus generated from the transfection was used to express cysteine synthase in Sf-9 insect cells using a multiplicity of infection (MOI) of 5 viral particles per insect cell in a 600 ml culture at a density of ~8×10$^5$ cells per milliliter. Infections were harvested after ~72 hours, and the cells pelleted by centrifugation. The cell pellets were lysed in 100 mM phosphate buffer, 300 mM NaCl, and 0.5% triton-100, by probe sonication (three 30 second bursts, on ice). The cell lysate was clarified by centrifugation at 15,000×g for 10 minutes.

The cysteine synthase was purified using the protocol described below.

Protein Purification Protocol: Clarified supernates from *E. coli* or baculovirus sources were incubated with Ni-agarose beads pre-washed with 100 mM phosphate buffer, pH 7.5, and 300 mM NaCl, for 30 minutes at 4° C. The supernate:bead mixture was then poured into a column. The supernate was allowed to flow through, and the beads were washed with 5 column volumes of wash buffer (100 mM phosphate buffer, pH 7.5, 300 mM NaCl, 20 mM imidazole). After washing, bound protein was eluted with 500 mM imidazole in 100 mM phosphate buffer, pH 7.5, and 10% glycerol. Fractions containing protein were pooled, final protein concentration determined by Bio-Rad protein determination reagent, and stored at −80° C.

Figure 3:
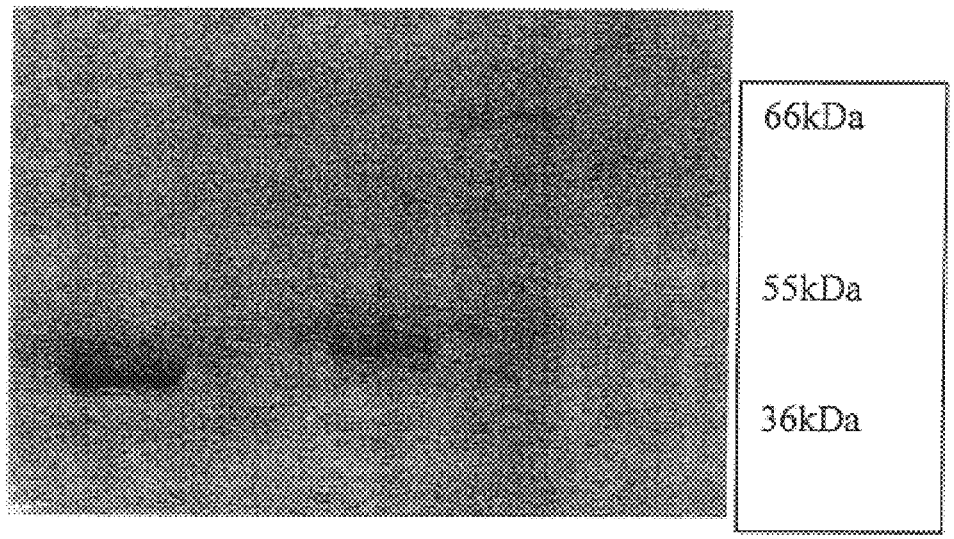
FIG. 3 is a Coomassie stained gel showing the elution of various fractions from the purification of cysteine synthase isolated from a baculovirus expression system. The lanes correspond to various fractions as indicated.

Cysteine synthase expressed using the baculovirus expression system was purified as described. The gel lanes correspond to the following samples: 1) elution. 2) column flow through. 3) pellet. 4) supernate. 5) molecular weight markers. (FIG. 3)

Figure 4:
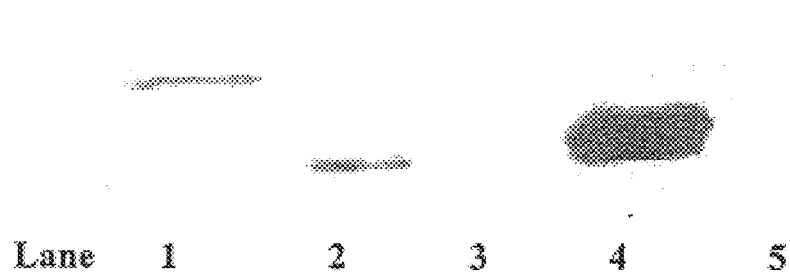
FIG. 4 is a western blot of cysteine synthase derived from the purification of the baculovirus expression of cysteine synthase, as shown in Example 1.

Samples from the baculovirus expression were probed with a mouse anti-penta-HIS antibody, and detected with a rabbit anti-mouse alkaline phosphatase conjugated secondary and NBT/BICP color reagent. Lane 1 is a HIS-tagged 50 kDa molecular weight marker, lane 2 is the supernate fraction from cells infected with recombinant cysteine synthase baculovirus, lane 3 is a supernate fraction from uninfected Sf-9 cells, lane 4 is the pellet fraction from cells infected with recombinant cysteine synthase baculovirus, lane 5 is the pellet fraction from uninfected Sf-9 cells. (FIG. 4)

The protein sequence of the cysteine synthase used in the assays described herein is identified above as SEQ ID NO 4.

Figure 5:
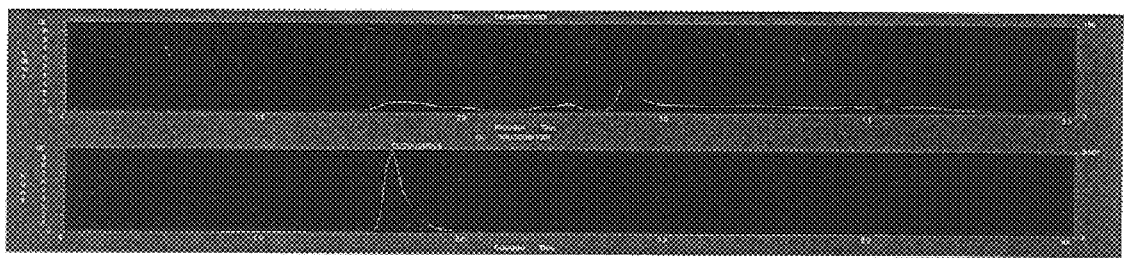
FIGS. 5a–5c are chromatograms resulting from the LC/MS analysis of cysteine synthase product formation. The top chromatogram in each of FIGS. 5a–c shows the analysis for cysteine, and the bottom chromatogram shows the analysis for O-acetyl-serine (OAS).
Figure 5:
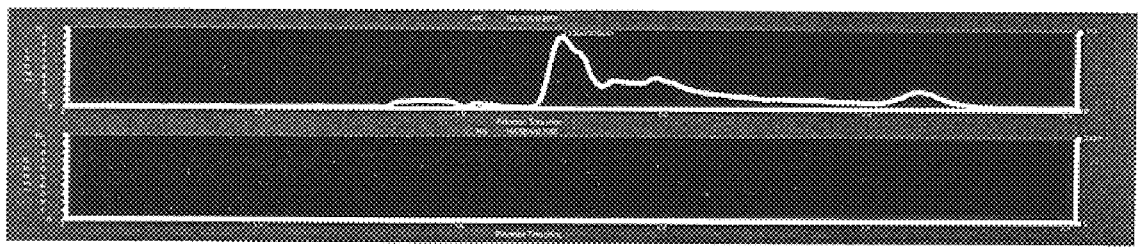
Figure 5:
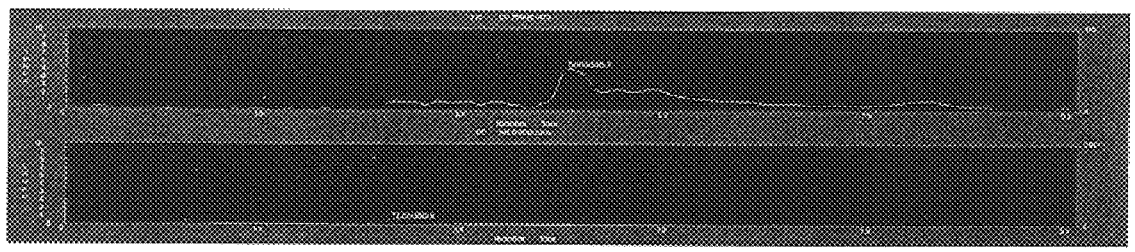

Cysteine synthase product formation was followed by LC/MS, as shown in FIGS. 5a–c. Samples were analyzed for cysteine (top panel in each of FIGS. 5a–c) and for OAS (bottom panels in each of FIGS. 5a–c). In the presence of enzyme, the substrate OAS was converted to cysteine. Cysteine synthase was reacted with 2 mM OAS and 2 mM sulfide, and the reactions were terminated by heating the mixtures to 90° C. for two minutes.

EXAMPLE 2

Cysteine Synthase HTS Protocol

Based on the experiments in a number of examples discussed below, optimum conditions for performing high throughput assays for cysteine synthase activity were determined. The optimum conditions are shown below, and the experiments that show how the optimum conditions were determined are shown in subsequent examples.

Assay buffer: O-Acetyl-L-serine (OAS) and sodium sulfide dissolved in 100 mM phosphate buffer, pH 7.5, at a concentration of 1.0 mM OAS and 0.2 mM sulfide.

Enzyme Solution: Purified cysteine synthase diluted in 100 mM phosphate buffer, pH 7.5, to a final concentration of 2.5 ng/µl.

Detection Solution: CPM dye (10 mg/ml stock in DMSO) diluted to 50 g/ml in a 50% DMSO solution.

Final Assay Concentrations: 100 mM phosphate buffer, pH 7.5, 0.5 mM OAS, 0.1 mM sulfide and 50 ng/well cysteine synthase.

Assay Protocol: All reagents were maintained at 40° C.

1) Add 25 µl/well of assay buffer to columns 5–24 by multidrop.
2) Add 25 µl/well of assay buffer containing 2% DMSO to columns one and two using a Tecan liquid handler (positive control).
3) Add 25 µl/well of assay buffer without OAS containing 2% DMSO to columns three and four using a Tecan liquid handler (negative control).
4) Add 5 µl/well of compounds to columns 5–24 using a cybi-well dispenser.
5) Add 20 µl/well of enzyme solution to the whole plate by multidrop.
6) Incubate for 30 minutes at room temperature.
7) Add 50 µl/well of Detection solution to all wells by multidrop.
8) Determine fluorescence at 340 exc./465emm. with a Tecan Ultra, in this example, at a gain of around 22.

Assay Plate: Greiner solid white, non-tissue culture treated 384 well plate.

Reagent List:
O-acetyl-L-serine: ICN cat# 105006
Sodium Sulfide: Sigma cat# S 4766
CPM: Molecular Probes cat# 346

EXAMPLE 3

Optimization of Cysteine Detection Using 7-diethylamino-3-(4-maleimidylphenyl)-4-methylcoumarin [CPM]

The purpose of this example was to optimize the detection of cysteine using the dye CPM. CPM was dissolved in DMSO to a concentration of 10 mg/ml. Working concentrations of dye were dissolved in a 50% DMSO solution to the indicated concentrations. Cysteine and sulfide were dissolved in 100 mM phosphate buffer, pH 7.5. The cysteine and sulfide solutions were added to white 384-well Greiner plates (50 µl/well), followed by an equal volume of CPM. Florescence at 360 excitation/460 emission was then measured using a Tecan Ultra. The optimal gain was determined with 1 mM cysteine and 50 µg/ml CPM, and this gain setting was used for all determinations.

Figure 6:
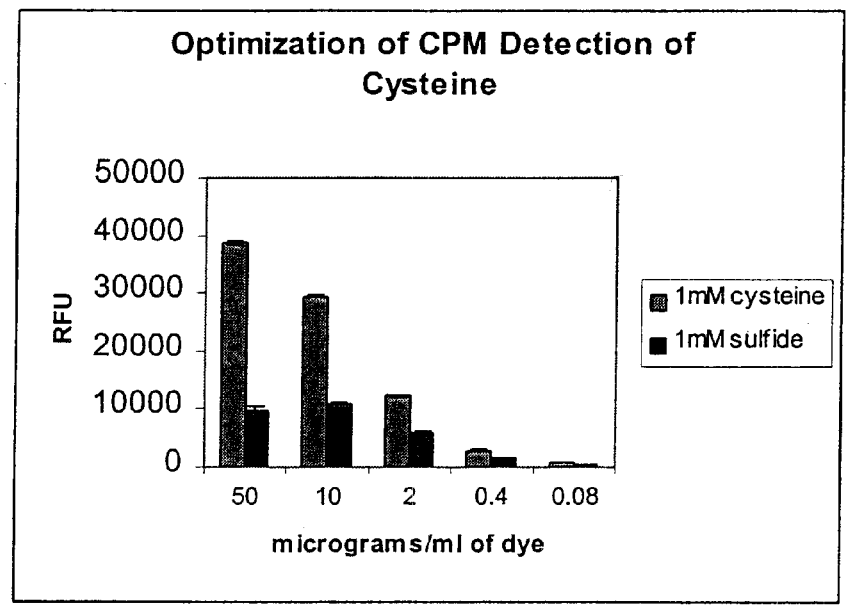
FIG. 6 is a bar graph showing the specific detection of cysteine over sulfide using 7-diethylamino-3-(4-maleimidylphenyl)-4-methylcoumarin (CPM), in relative fluorescence units (RFU) versus µg/ml CPM. Gray bars represent 1 mM cysteine, and dark bars represent 1 mM sulfide.

The results of the optimization are shown in FIG. 6. The values shown are the mean of triplicate determinations, and the standard deviation is indicated. The data show that with the difference in fluorescence between the sulfide and the cysteine is greatest with relatively higher concentrations (50 µg/ml CPM) than with relatively lower concentrations (0.08 µg/ml CPM) of CPM.

Figure 7:
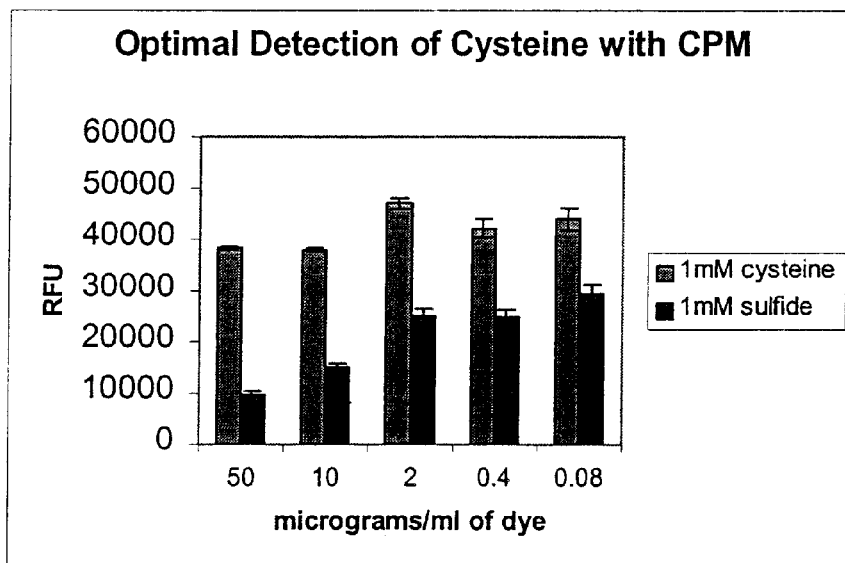
FIG. 7 is a bar graph showing the optimal detection of cysteine using CPM, in RFU versus µg/ml CPM. Gray bars represent 1 mM cysteine, and dark bars represent 1 mM sulfide.

A second optimization experiment was performed using the assay conditions described above, but for each dye concentration, the optimal gain was re-set on 1 mM cysteine. The results of the optimization are shown in FIG. 7. The values shown are the mean of triplicate determinations, and the standard deviation is indicated. This data also shows that the difference in fluorescence between the sulfide and the cysteine is greatest with relatively higher concentrations (50 μg/ml CPM) than with relatively lower concentrations (0.08 μg/ml CPM) of CPM.

EXAMPLE 4

Stability of CPM Solutions

Figure 8:
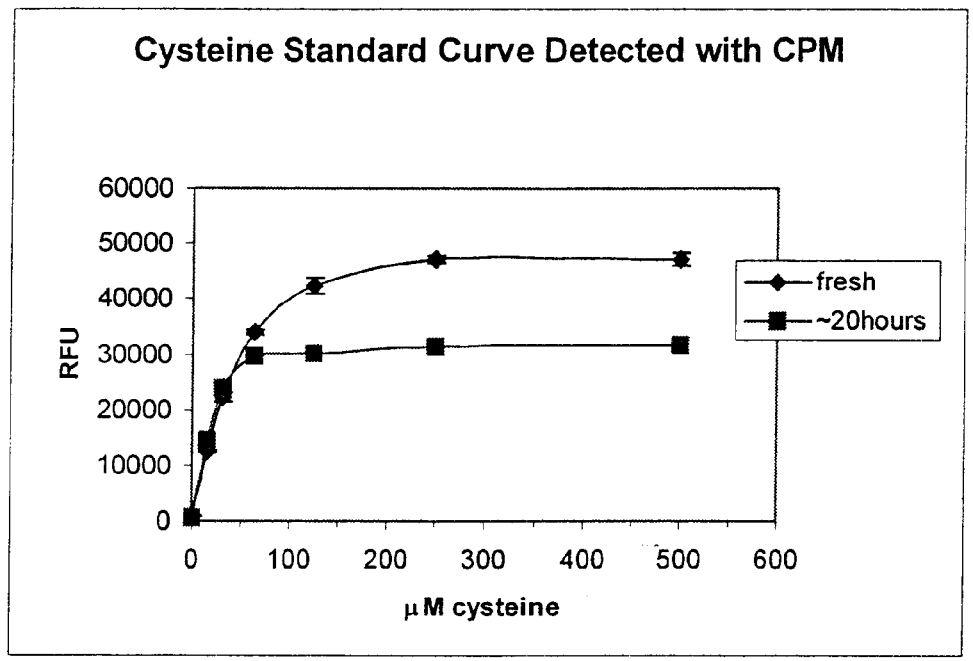
FIG. 8 is a standard curve comparing the detection of cysteine using fresh CPM (diamonds) and CPM aged for 20 hours (squares), in RFU versus µM cysteine.

An experiment was performed to determine the stability of CPM solutions, where the solutions were a 50/50 mixture of water and dimethyl sulfoxide (DMSO) and had a CPM concentration of 50 μg/ml. A cysteine standard curve was prepared with various concentrations of cysteine in a 100 mM phosphate buffer solution and contacted with fresh CPM solution and a CPM solution that had been stored in the dark for 20 hours at room temperature. The data, shown in FIG. 8, show that there is a change in measured fluorescence between the cysteine/CPM conjugate formed by the fresh solution and the stored solution when the concentration of cysteine exceeded about 50 μM. The values obtained using the fresh CPM solution are in triplicate, and the standard deviation is indicated. The values obtained using the 20 hour old CPM solution are in duplicate.

Figure 9:
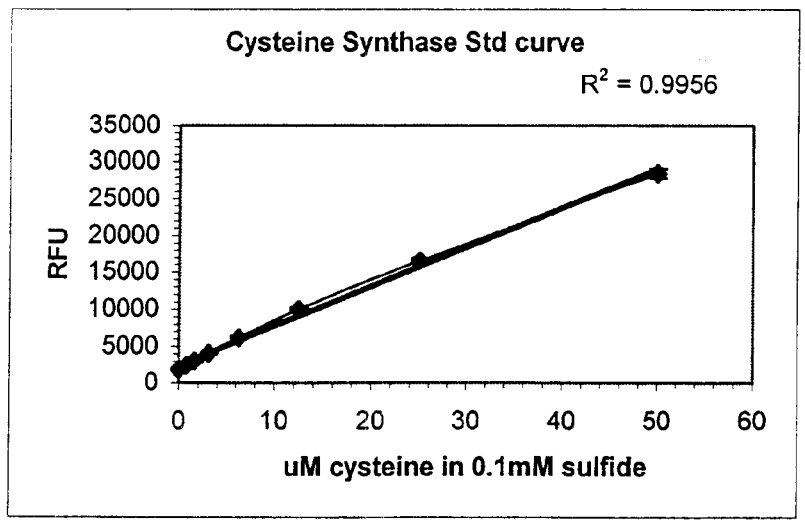
FIG. 9 is a standard curve showing the detection of cysteine in the presence of 50 µg/ml CPM, in RFU versus µM cysteine in 0.1 mM sulfide.

The experiment shown in FIG. 8 was repeated using a cysteine standard curve that included 0.1 mM sulfide in the 100 mM phosphate buffer. Concentrations of cysteine were kept at or below about 50 μM, the point at which there was an observed difference between the fresh and stored solutions. The results are shown in FIG. 9. The values are the mean of triplicate determinations, and the standard deviation is indicated. The experiment was repeated several times. The data show a roughly linear correlation between cysteine concentration and fluorescence over this concentration range, even in the presence of sulfide.

EXAMPLE 5

Comparison of Fluorescence of Cysteine/CPM and OAS

Figure 10:
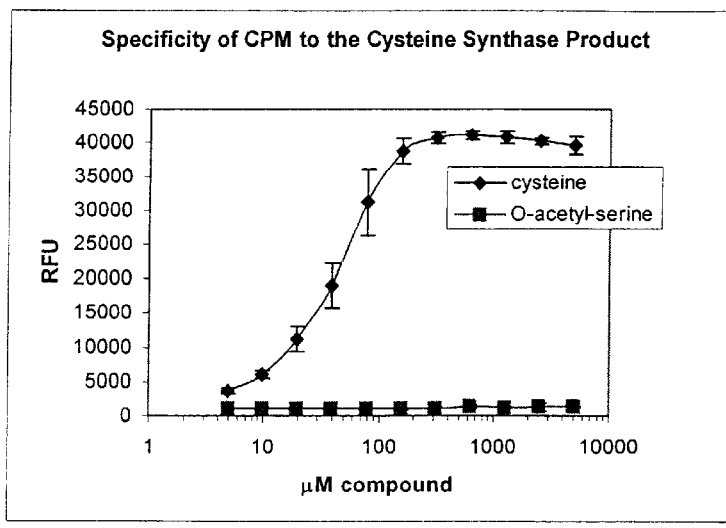
FIG. 10 is a graph representing the specificity of CPM to cysteine versus O-acetyl serine (OAS) in RFU versus µM concentration of either cysteine or OAS. Diamonds represent cysteine, and squares represent OAS.

An experiment was performed to compare the fluorescence of cysteine and O-acetyl serine ("OAS", the cysteine precursor) in the presence of CPM. Solutions of cysteine and O-acetyl-serine at various concentrations were prepared in a 100 mM phosphate buffer solution that included 50 μM sulfide. The solutions were placed in various wells in a multi-well plate. An equal volume of 50 μg/ml CPM was then added to each well. The fluorescence was measured, and the data is shown in FIG. 10. The values are the mean of triplicate determinations, and the standard deviation is indicated. The data clearly show that there is virtually no fluorescence for O-acetyl serine in the presence of CPM and sulfide, whereas there is measurable fluorescence for cysteine in the presence of CPM and sulfide.

Accordingly, this data shows that CPM is an effective dye for use in detecting the presence of cysteine in the presence of both O-acetyl serine and sulfide. Since O-acetyl serine and sulfide react in the presence of a viable cysteine synthase to form cysteine, the viability of the cysteine synthase (i.e., the ability to form cysteine) can be measured using the complex of CPM and cysteine. Further, the viability of a cysteine synthase in the presence of a test compound can be measured and compared to the viability of the synthase in the absence of the test compound by measuring the fluorescence of a cysteine/CPM conjugate.

EXAMPLE 6

Formation of Cysteine by Cysteine Synthase Measured Using Ninhydrin

Figure 11:
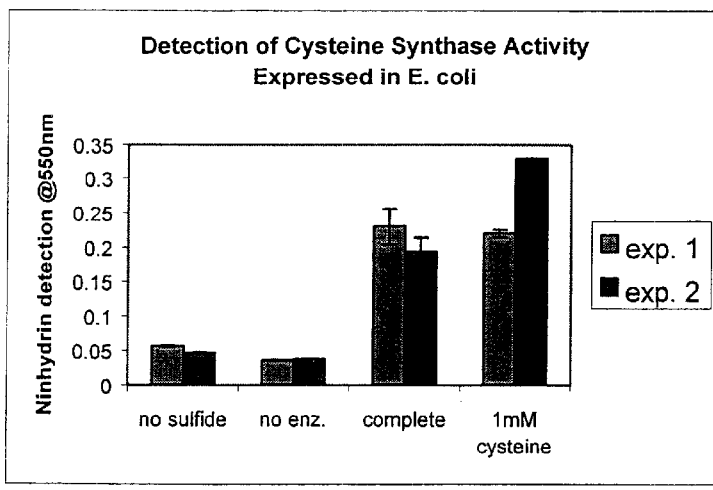
FIG. 11 is a bar graph showing the detection of cysteine synthase activity expressed in E. coli, as measured by ninhydrin detection at 550 nm. The gray bars represent the results from a first experiment, and the dark bars represent the results from a second experiment.

The formation of cysteine by a cysteine synthase was measured using a ninhydrin reagent. In this experiment, purified cysteine synthase protein diluted 1:10 was tested for activity with 1 mM OAS and 1 mM sulfide in 100 mM phosphate buffer (pH 7.5) with a total volume of 500 μl. The mixture was incubated for one hour at 37° C. After incubation, an equal volume of ninhydrin reagent (62.5 mg ninhydrin, 1 mL concentrated HCl, 4 mL concentrated acetic acid and 5 mL) was added to each tube. An additional 10 minute incubation at 95° C. was then performed to allow the ninhydrin to react. Three 100 μl samples from each reaction tube were then transferred to a 384 well plate, and the absorbance at 550 nm was determined. The data is shown in FIG. 11. The values are the mean of three values, with the standard deviation indicated. The experiment was performed twice.

EXAMPLE 7

Comparison of Results Obtained Using Different Cysteine Synthases

Figure 12:
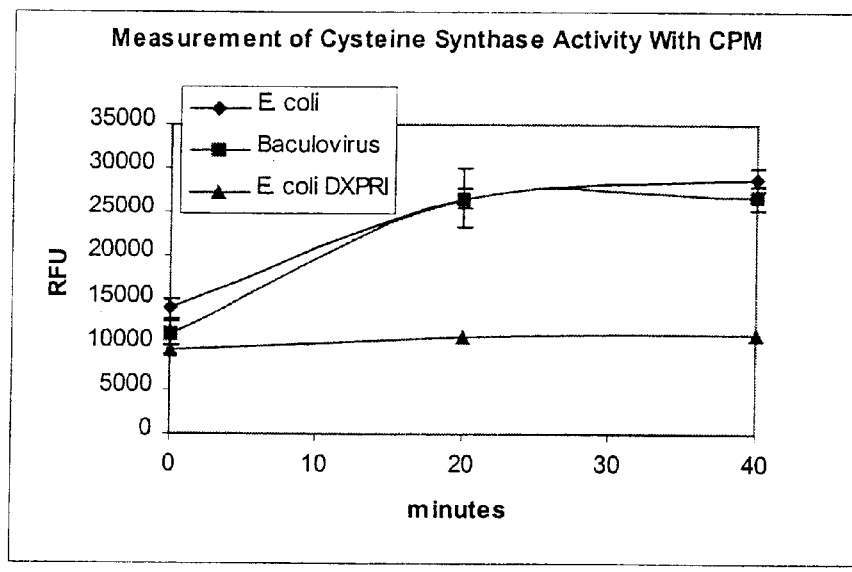
FIG. 12 is a graph showing the detection of recombinant cysteine synthase activity from both E. coli (diamonds) and baculovirus sources (squares), as compared to another protein from E. coli (DXPRI, represented by the triangles), in RFU versus time in minutes.

To verify that the assay method is general for cysteine synthase from more than one source, an experiment was performed where recombinant protein from both E. coli and baculovirus were test for activity using CPM to detect the formation of cysteine. 5 μg/well or protein was assayed in 100 mM phosphate buffer (pH 7.5) that included 0.5 mM sulfide and 0.5 mM OAS at room temperature. The cysteine formed was measured by complexation with CPM and fluorescence detection. To show that the activity was specific to cysteine synthase, another HIS-tagged protein (DXPRI) was also assayed. The data is shown in FIG. 12, where the values for recombinant synthase activity are the result of triplicate determinations, and DXPRI was tested in duplicate. Standard deviations are indicated. As shown in FIG. 12, substantially the same results were obtained using recombinant cysteine synthase from different sources.

EXAMPLE 8

Determination of Optimum Sulfide Concentration

Figure 13:
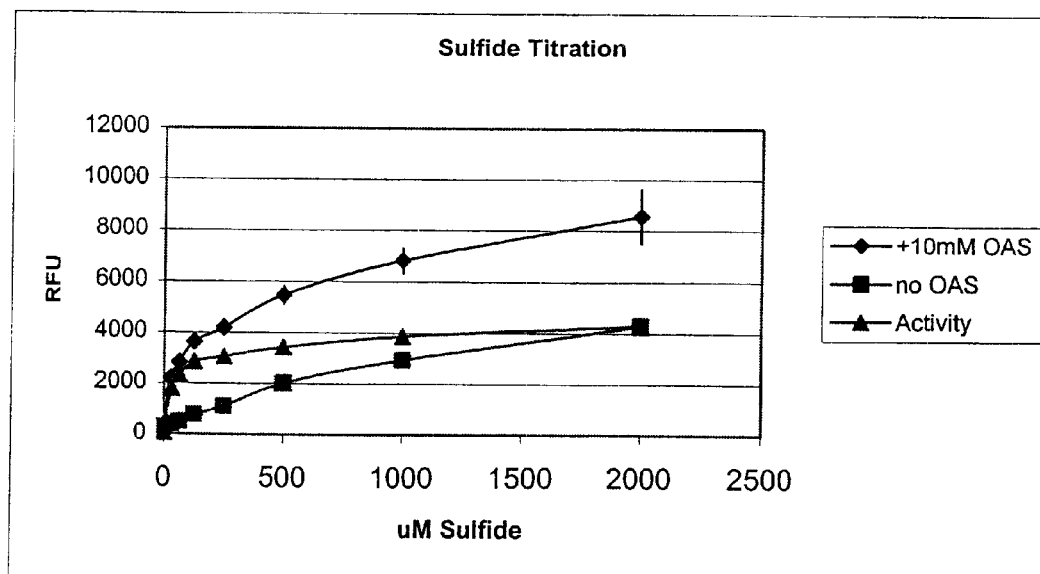
FIG. 13 is a graph showing a titration of sulfide concentration, in RFU versus micrimolar sulfide concentration. Diamonds represent the assay with 10 mM OAS and various sulfide concentrations, squares represent results with various sulfide concentrations but where no OAS was added, and triangles represent the difference in RFU+/−OAS at the different sulfide concentrations. The graph shows that increasing at sulfide concentrations, there is an increase in background RFU, and optimum assay results are observed using a sulfide concentration of 0.5 mM.

An experiment was performed to determine the optimum sulfide concentration. The sulfide concentration was titrated while maintaining a constant concentration of OAS at 10 mM. The protein (cysteine synthase) concentration was kept constant at 1 μg/well, and all solutions were made in 100 mM phosphate buffer (pH 7.5). The contents of the assay were incubated at room temperature for 25 minutes. Cysteine concentrations were determined with 50 μg/mL CPM dye. The results are shown in FIG. 13. All values are the mean of triplicate determinations, where the error bars indicate standard deviations.

EXAMPLE 9

Determination of Optimum OAS Concentration

Figure 14:
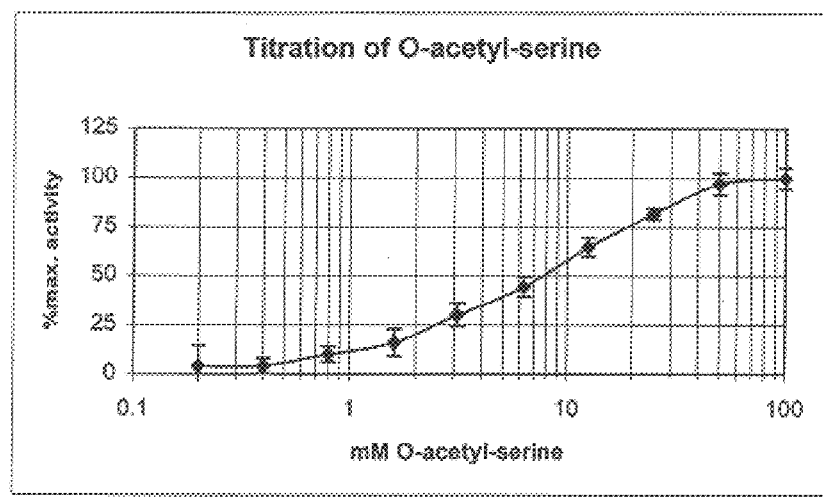
FIG. 14 is a graph showing the determination of optimal OAS concentration, in terms of percent maximum activity versus mM OAS.

An experiment was performed to determine the optimum OAS concentration. The OAS concentration was titrated while maintaining a constant concentration of sulfide at 0.5 mM. The protein (cysteine synthase) concentration was kept constant at 1 μg/well, and all solutions were made in 100 mM phosphate buffer (pH 7.5). The contents of the assay were incubated at room temperature for 25 minutes. Cysteine concentrations were determined with 50 μg/mL CPM dye. The results are shown in FIG. 14. All values are the mean of triplicate determinations, where the error bars indicate standard deviations.

EXAMPLE 10

Determination of Optimum Cysteine Synthase Concentration

Figure 15:
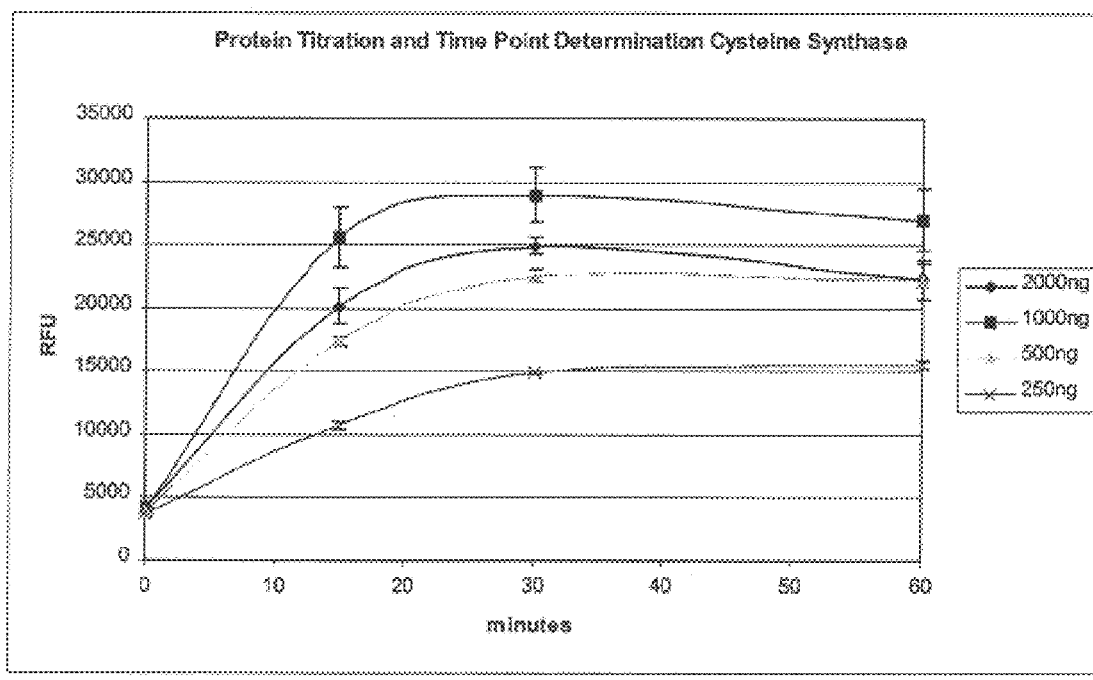
FIG. 15 is a graph showing the protein titration (cysteine concentration) and time point determination of cysteine synthase, in RFU versus time in minutes. Diamonds represent a cysteine concentration.

An experiment was performed where differing amounts of cysteine synthase were assayed for cysteine synthase activity in 100 mM phosphate buffer (pH 7.5) containing 0.5 mM sulfide and 50 mM OAS. Cysteine concentration at various time points was determined with 50 μg/mL CPM dye in 50% DMSO by volume. The data show that the reactions were essentially complete by 30 minutes, as determined by a relatively constant fluorescence of the cysteine/CPM conjugate, regardless of the enzyme concentration. The results are shown in FIG. 15, where the values represent the mean of triplicate determinations, and where the standard deviation is shown. The experiment was repeated several times.

EXAMPLE 11

Effect of Limiting Sulfide on the Analysis

Figure 16:
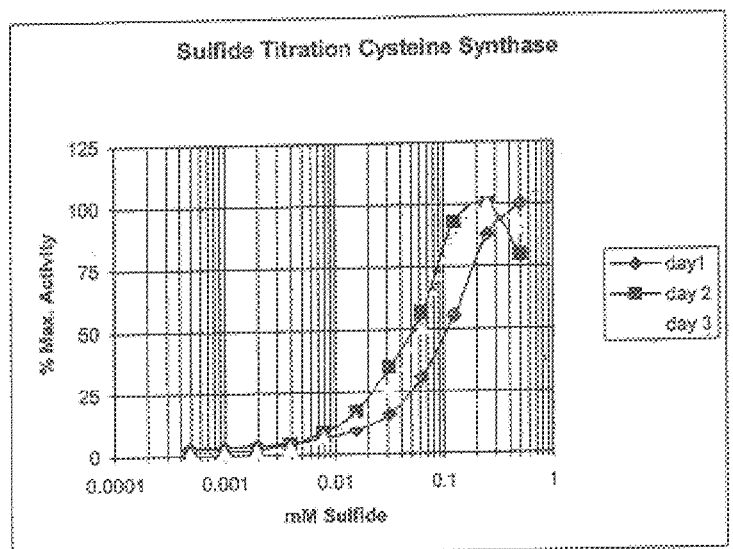
FIG. 16 is a graph showing the determination of sulfide concentration, in terms of percentage of maximum activity versus mM sulfide concentration. The diamonds represent results obtained on a first day, the squares represents the results obtained on a second day, and the triangles represent results obtained on a third day.

An experiment was performed using a limiting amount of sulfide. A 1:100 molar ratio of sulfide to OAS was prepared and diluted at a 1:1 ratio with phosphate buffer. A sulfide concentration was determined for cysteine synthase, which gave a value that was approximately 50% of the maximum value of the assay. The reactions were performed for 30 minutes at room temperature in 100 mM phosphate buffer (pH 7.5), with 0.5 μg/well cysteine synthase, which, as discussed above, are the conditions at which the reaction would be expected to be substantially complete. Cysteine was measured using a 50 μg/ml CPM concentration. Non-specific RFU were determined with sulfide alone plus protein and subtracted from the RFU obtained in the presence of OAS. The results are shown in FIG. 16, where the data shown is the mean of triplicate determinations, and the experiment was repeated three separate times.

Figure 17:
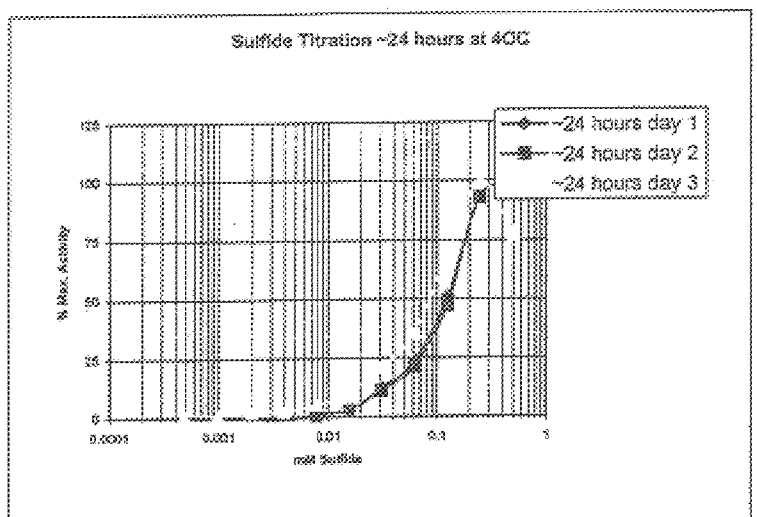
FIG. 17 is a graph showing the sulfide titration for cysteine synthase after it was stored at 4° C. for approximately 24 hours, in percent maximum activity versus mM sulfide. The diamonds represent results obtained on a first day, the squares represents the results obtained on a second day, and the triangles represent results obtained on a third day.

The experiment above was repeated using reagents that were stored for about 24 hours at about −4° C. The results are shown in FIG. 17, with the values shown being the mean of triplicate determinations and the experiments repeated three separate times. Based on all six experiments, an average of 0.1 mM sulfide gave a value of about 50% of the maximum specific signal determined for cysteine synthase. This concentration was used for further experiments.

EXAMPLE 12

Effect of Varying OAS Concentrations

Figure 18:
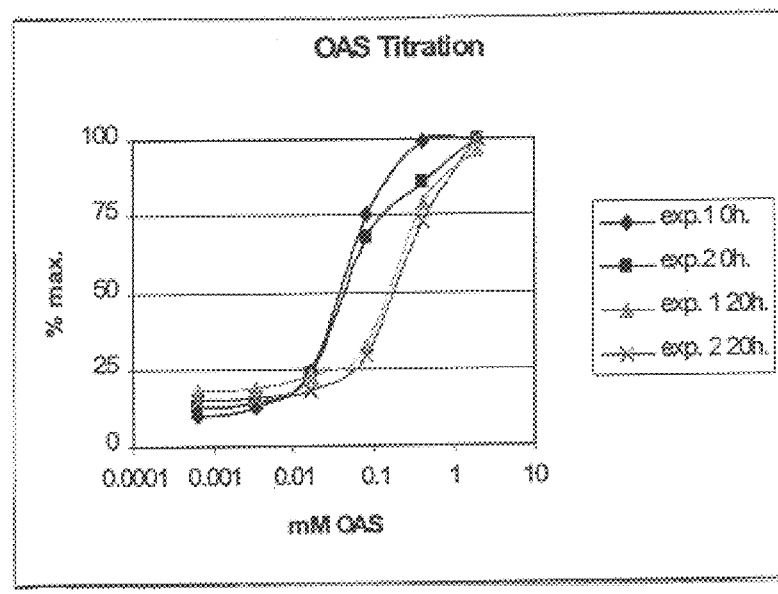
FIG. 18 is a graph showing an OAS titration, in percent maximum activity versus mM sulfide. The diamonds represent results of a first experiment with fresh reagents, the squares represent the results of a repeat experiment with fresh reagents, the triangles represent results of the first experiment with reagents aged for approximately 20 hours at 4° C., and the dashed line represents results of the second experiment with reagents aged for approximately 20 hours at 4° C.

Another experiment was performed to titrate the OAS concentration. Holding the concentration of sulfide constant at 0.1 mM, the concentration of OAS was titrated. This experiment was performed four separate times, twice with freshly prepared reagents, twice with the same reagents stored at 4° C. for about 20 hours. The results are shown in FIG. 18, with the values representing the mean of triplicate determinations. The results show that there are slight differences observed at certain concentrations when the reagents are stored for extended periods of time.

EXAMPLE 13

Figure 19:
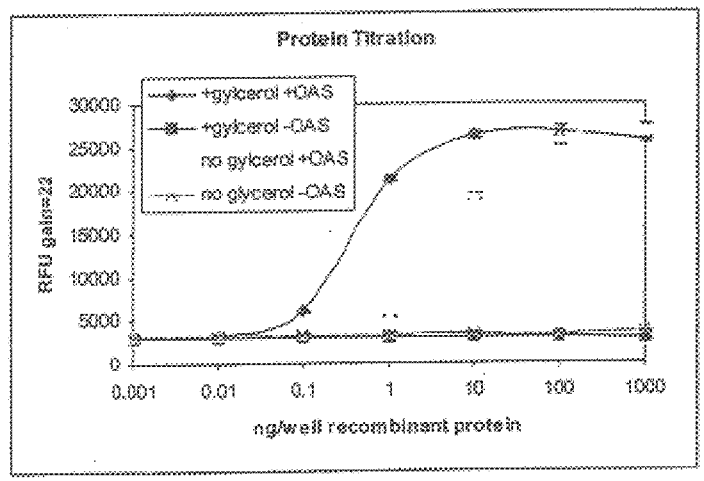
FIG. 19 is a graph showing the protein titration and storage conditions for recombinant cysteine synthase in RFU versus ng/well recombinant protein. Diamonds represent results with glycerol and OAS added. The squares represent results with glycerol but no OAS added. The triangles represent results where OAS but no glycerol was added, and the dashed line represents results where neither glycerol or OAS was added.

Effect of Varying Cysteine Synthase Concentration and Evaluation of Storage Conditions for Recombinant Cysteine Synthase Using the optimum values for OAS concentration, sulfide concentration, buffer, reaction time and reaction temperature obtained in the preceding experiments, an assay was performed to evaluate protein titration and storage conditions for recombinant cysteine synthase. Two separate protein purifications were performed from *E. coli* expressing recombinant cysteine synthase. The purifications were both performed using the same protocol, except that 10% glycerol was included in the elution buffer of one of the solutions. Fractions containing protein were frozen at −80° C. until the protein was used in the assay. Protein concentrations were determined using a Bio-Rad protein determination reagent. Enzyme samples were diluted in 100 mM phosphate buffer to the desired concentration and assayed in 100 mM phosphate buffer (pH 7.5), containing 1.0 mM sulfide, 50 mM OAS, for 30 minutes at room temperature. One experiment included both glycerol and OAS, one included glycerol but no OAS, one included OAS but no glycerol, and one included no glycerol and no OAS. The results are shown in FIG. 19, which shows the mean of triplicate determinations and shows the standard deviation. Each experiment was performed twice. The data show that glycerol is an effective agent for preserving the cysteine synthase while it is stored, and that a low baseline RFU value is observed when there is no OAS present to convert to cysteine.

EXAMPLE 14

Determination of Km Values for Recombinant Cysteine Synthase

Figure 20:
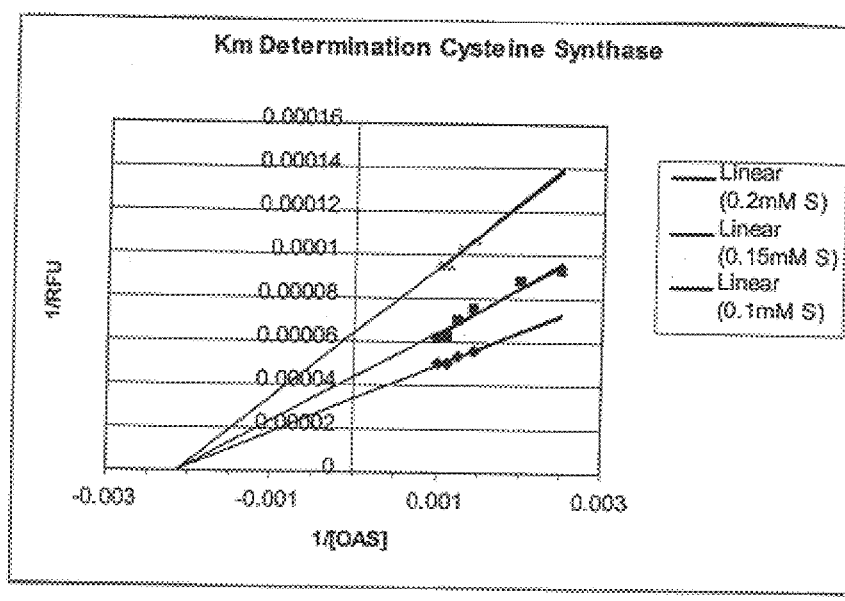
FIG. 20 is a graph showing the Km determination for recombinant cysteine synthase, in terms of 1/RFU versus 1/[$\mu$M OAS].

The Km value for recombinant cysteine synthase was determined by titrating OAS in different sulfide concentrations. The assay was performed in white 96 well plates, with 100 μl of reaction mixture containing 60 ng/well cysteine synthase. The assay contents were incubated for 30 minutes at room temperature. The amount of cysteine formed was determined with an equal volume of CPM dye. The apparent Km is about 0.5 mM for OAS. This experiment was performed twice, and the values are the mean of duplicate determinations. The results are shown in FIG. 20.

EXAMPLE 15

Evaluation of the Assay Under High Throughput Conditions

Figure 21:
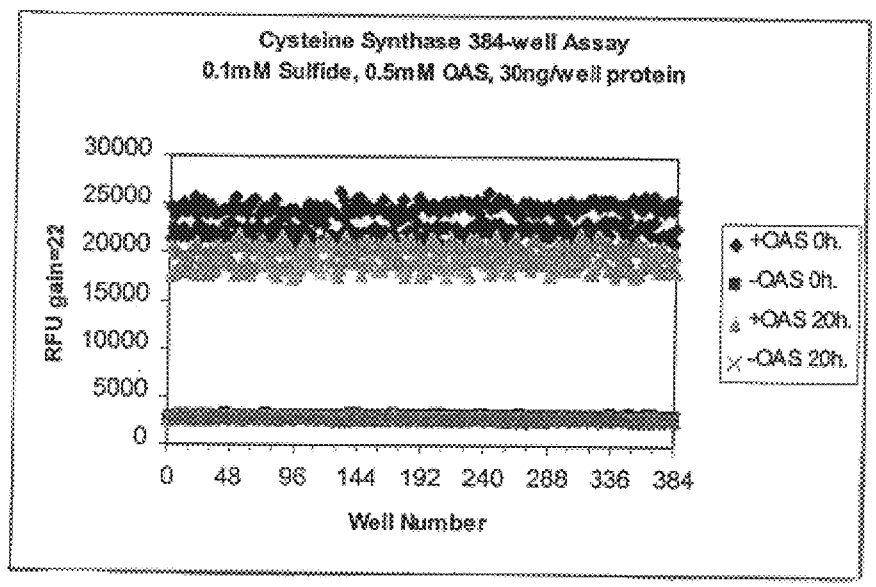
FIG. 21 is a graph showing the results of a high throughput cysteine synthase assay, in terms of RFU (measured with a gain setting of 22) versus well number. The diamonds represent results obtained with fresh reagents and OAS added. The squares represent results obtained with fresh reagents and no OAS added. The triangles represent results obtained with reagents aged for approximately 20 hours at 4° C. with OAS added and the dashed line represents results obtained with aged reagents with no OAS added.

The cysteine synthase assay was tested for compatibility with the Bayer HTS system. The assay was performed in 100 mM phosphate buffer (pH 7.5), with a final concentration of 0.1 mM sulfide, 0.5 mM OAS and 30 ng/well cysteine synthase. The assay contents were incubated at room temperature for 30 minutes. The cysteine formed was detected using CPM dye. All additions were performed using a Multidrop apparatus. For the 20-hour assay time-point, all reagents were stored at 4° C., with the exception of the dye, which was stored in the dark at room temperature. A Tecan Ultra was used to detect the fluorescence, with settings of one read per well with 0 seconds between reads, gain −22. Z factors were 0.77 for the 0 hour reagents, 0.80 for the 20 hour old reagents. The results are shown in FIG. 21. As shown in the figure, all results where OAS was present were substantially identical, regardless of whether the reagents were fresh or stored. All results where OAS was not present were also substantially identical, regardless of whether the reagents were fresh or stored.

EXAMPLE 16

Figure 22:
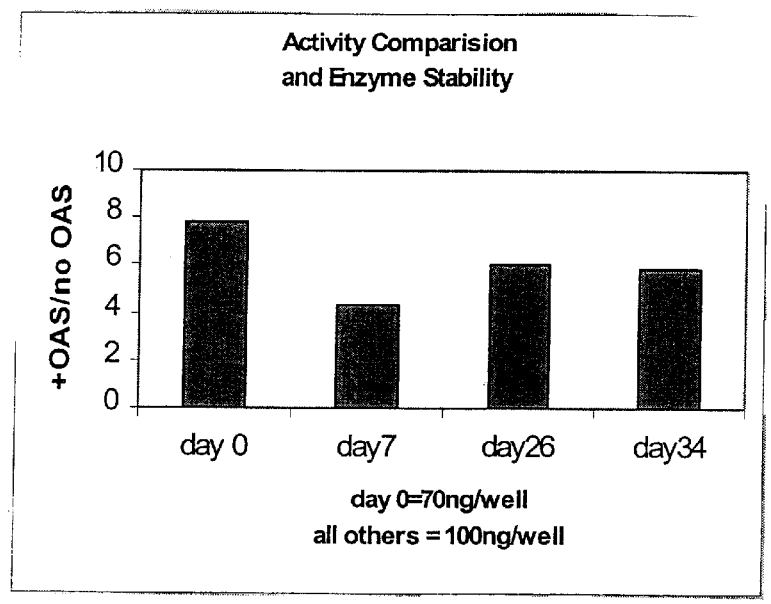
FIG. 22 is a bar graph comparing the results of enzyme activity, in terms of the ratio of specific and non-specific cysteine formation (OAS added/OAS not added), on day 0, 7, 26 and 34.

Evaluation of Enzyme Stability Over Time and Under Different Storage Conditions While performing the assay validation experiments, it was noted that there was a drop in enzyme activity over time. To determine the long term stability and activity of cysteine synthase, a fresh purification from *E. coli* was performed and the enzyme activity studied over time. Protein was stored in 10% glycerol at −80° C. The data is shown in FIG. 22, where the values shown are the ratio between specific cysteine formation (in the presence of OAS) and non-specific cysteine formation (in the absence of OAS). All experiments were performed in triplicate. On day 0, the concentration of cysteine synthase was 70 ng/well, and on other days, the concentration was 100 ng/well. The results show a decline in activity between day 0 and day 7, followed by an increase in activity between day 7 and 26 (although there Was still less activity than observed on day 0), with the activity roughly the same on days 26 and 34.

Figure 23A:
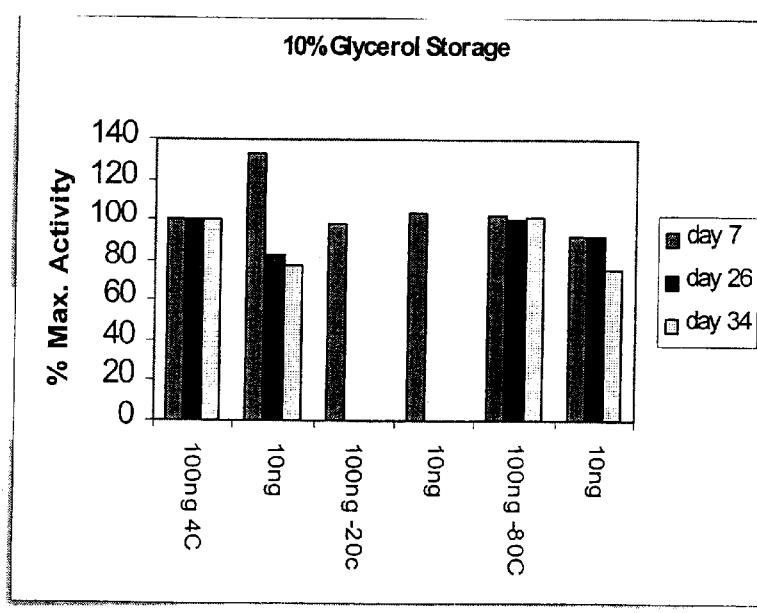
FIGS. 23a–23c are bar graphs showing the percent activity of the cysteine synthase enzyme (% max. activity) at various conditions of temperatures, concentrations of glycerol and storage times. Shaded bars represent day 7, dark bars represent day 26 and clear bars represent day 34.
Figure 23B:
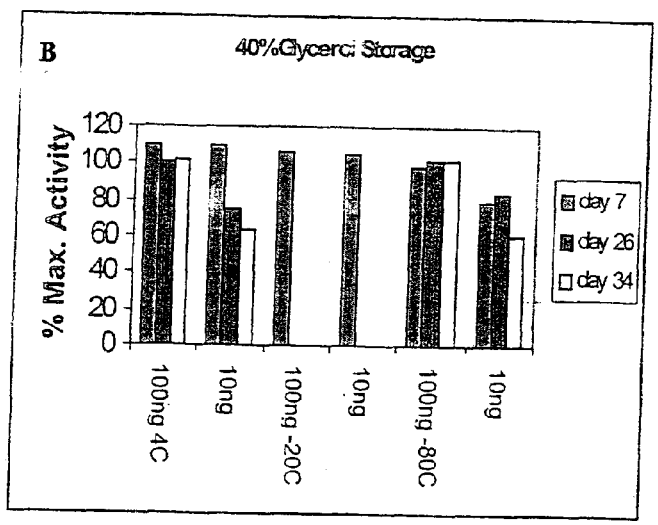
Figure 23C:
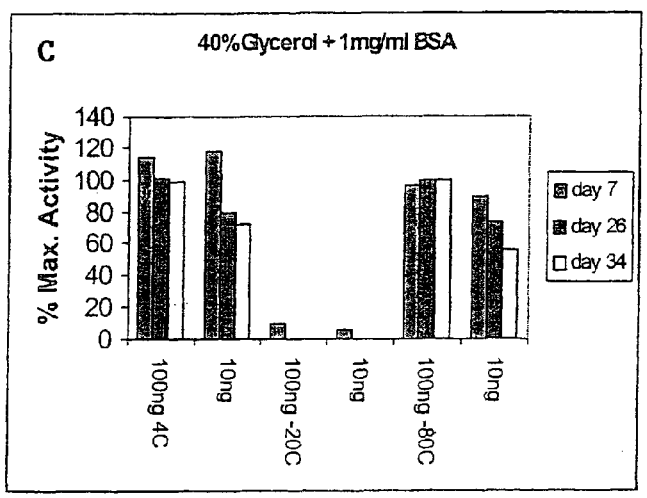

The stability of cysteine synthase in different storage conditions was evaluated. The storage conditions included 10% glycerol, 40% glycerol and 40% glycerol and 1 mg/ml bovine serum albumin (BSA). Assays were run on different days after storage with +/−0.5 mM OAS and 0.1 mM sulfide. Assays were performed in triplicate, non-specific RFU counts were subtracted from specific RFU counts, and all counts were normalized against the activity of 100 ng/well protein stored at 4° C. The results are shown in FIGS. 23*a–c*. Based on this data, it may be preferable to purify the protein less than 3 weeks for use, and store it at a relatively cold temperature (for example, around −80° C.) with 10% glycerol, and assay the protein at about 50 ng/well.

Figure 24:
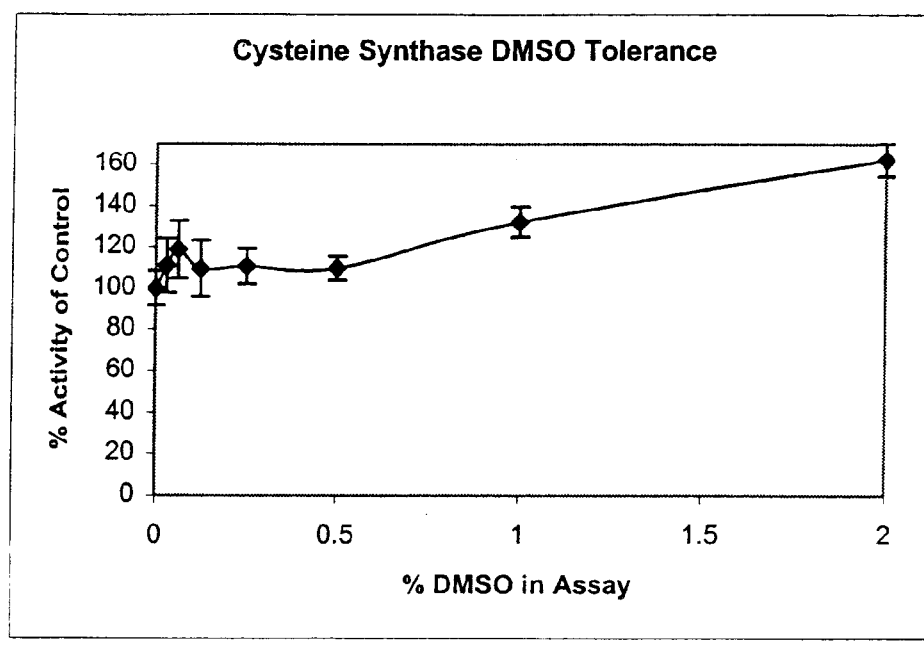
FIG. 24 is a graph showing the assay tolerance of DMSO, in terms of percent activity of control versus percent DMSO in the assay.

A cysteine synthase assay was performed using various amounts of DMSO to test the assay compatibility of the DMSO. The results are shown in FIG. 24, where all values are the mean of triplicate determinations, and standard deviations are indicated. No inhibitory effect of DMSO was observed over the concentrations tested, and there was in fact a slight increase in activity as the concentration of DMSO increased from 0 to 2% (by volume).

While the foregoing describes certain embodiments of the invention, it will be understood by those skilled in the art that variations and modifications may be made and still fall within the scope of the invention.

What is claimed is:

1. A method for determining cysteine synthase activity, comprising:
    a) combining O-acetyl-L-serine, sulfide and cysteine synthase to form a reaction mixture under conditions suitable for the production of cysteine;
    b) contacting said reaction mixture with a coumarin dye capable of conjugating with cysteine; and
    c) subjecting the reaction mixture from step (b) to UV light and detecting fluorescent light emission.

2. The method of claim 1, wherein the dye is CPM or DACM.

3. The method of claim 1, wherein said cysteine synthase is a plant cysteine synthase.

4. The method of claim 3, wherein said plant cysteine synthase is an Arabidopsis cysteine synthase.

5. The method of claim 4, wherein Arabidopsis cysteine synthase has the amino acid sequence of SEQ ID NO 4.

6. The method of claim 2, wherein the wavelength of said UV light is approximately 330–350 nm and the wavelength of said fluorescent light emission is approximately 465 nm.

7. The method of claim 2, wherein said contacting is with 10–100 µg/ml CPM.

8. The method of claim 2, wherein said O-acetyl-L-serine is present in said reaction mixture at an initial concentration of 0.1–5.0 mM, and said sulfide is present in said reaction mixture at an initial concentration of 0.01–1.0 mM.

9. The method of claim 8, wherein said reaction mixture further comprises 75–150 mM phosphate buffer at a pH of 7.0–8.0.

10. A method for identifying a test compound as a herbicide candidate, comprising:
    a) combining O-acetyl-L-serine, sulfide and cysteine synthase to form a reaction mixture in the presence and absence of said test compound;
    b) contacting said reaction mixture with a coumarin dye capable of conjugating with cysteine;
    c) subjecting the reaction mixture from step (b) to UV light and detecting fluorescent light emission; and
    d) comparing the amount of said fluorescent light emission in the presence and absence of said test compound; wherein a decrease in the amount of said fluorescent light emission in the presence of said test compound indicates that said test compound is a herbicide candidate.

11. The method of claim 10, wherein the dye is CPM or DACM.

12. The method of claim 10, wherein said cysteine synthase is a plant cysteine synthase.

13. The method of claim 12, wherein said plant cysteine synthase is an Arabidopsis cysteine synthase.

14. The method of claim 13, wherein Arabidopsis cysteine synthase has the amino acid sequence of SEQ ID NO 4.

15. The method of claim 13, wherein the wavelength of said UV light is approximately 330–350 nm and the wavelength of said fluorescent light emission is approximately 465 nm.

16. The method of claim 13, wherein said contacting is with 10–100 µg/ml CPM.

17. The method of claim 13, wherein said O-acetyl-L-serine is present in said reaction mixture at an initial concentration of 0.1–5.0 mM, and said sulfide is present in said reaction mixture at an initial concentration of 0.01–1.0 mM.

18. The method of claim 11, wherein said reaction mixture further comprises 75–150 mM phosphate buffer at a pH of 7.0–8.0.

19. A method for identifying compounds capable of selectively inhibiting plant, fungal and/or bacterial cysteine synthase activity, comprising:
    a) combining O-acetyl-L-serine, sulfide and a plant cysteine synthase to form a reaction mixture under conditions suitable for the production of cysteine;
    b) contacting said reaction mixture with a coumarin dye capable of conjugating with cysteine;
    c) subjecting the reaction mixture from step (b) to UV light and detecting fluorescent light emission,
    d) determining the inhibitory activity of the compound based on the fluorescent light emission,
    e) repeating steps a–d using a fungal or bacterial cysteine synthase, and
    f) identifying compounds that selectively inhibit plant, fungal or bacterial cysteine synthase.

20. The method of claim 19, wherein the dye is CPM or DACM.

21. The method of claim 19, wherein said cysteine synthase is a plant cysteine synthase.

22. The method of claim 21, wherein said plant cysteine synthase is an Arabidopsis cysteine synthase.

23. The method of claim 22, wherein Arabidopsis cysteine synthase has the amino acid sequence of SEQ ID NO 4.

24. The method of claim 20, wherein the wavelength of said UV light is approximately 330–350 nm and the wavelength of said fluorescent light emission is approximately 465 nm.

25. The method of claim 20, wherein said contacting is with 10–100 µg/ml CPM.

26. The method of claim 20, wherein said O-acetyl-L-serine is present in said reaction mixture at an initial concentration of 0.1–5.0 mM, and said sulfide is present in said reaction mixture at an initial concentration of 0.01–1.0 mM.

27. The method of claim 20, wherein said reaction mixture further comprises 75–150 mM phosphate buffer at a pH of 7.0–8.0.

* * * * *